United States Patent [19]
Tabuchi et al.

[11] Patent Number: 5,912,330
[45] Date of Patent: Jun. 15, 1999

[54] CRYSTALLINE MALTOSYL GLUCOSIDE, AND ITS PRODUCTION AND USE

[75] Inventors: Akihiko Tabuchi; Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 08/933,929

[22] Filed: Sep. 19, 1997

Related U.S. Application Data

[63] Continuation of application No. 08/717,746, Sep. 23, 1996, abandoned, which is a continuation of application No. 08/396,747, Mar. 1, 1995, abandoned.

[30] Foreign Application Priority Data

Mar. 1, 1994 [JP] Japan .................................. 6-054369

[51] Int. Cl.$^6$ ............................... C12P 19/44; C07H 3/06
[52] U.S. Cl. .................. 536/4.1; 536/123.1; 536/123.13; 536/127; 435/72; 435/96; 435/97; 435/98; 435/99; 435/101; 435/74
[58] Field of Search .................................. 536/4.1, 123.1, 536/123.13, 127; 435/72, 96, 97, 98, 99, 101, 74

[56] References Cited

U.S. PATENT DOCUMENTS 5,322,693  6/1994  Shibuya et al. ......................... 424/439

FOREIGN PATENT DOCUMENTS

| 0480640 | 4/1992 | European Pat. Off. . |
| 0606753 | 7/1994 | European Pat. Off. . |
| 0628630 | 12/1994 | European Pat. Off. . |
| 0023799 | 2/1983 | Japan . |
| 0148794 | 8/1984 | Japan . |
| 2106912 | 4/1993 | United Kingdom . |
| WO92/03565 | 5/1992 | WIPO . |

OTHER PUBLICATIONS

Ajisaka et al, Carbohydr. Res. 199:227–234 (1990).
Hendrix et al, Carbohydr. Res. 253:329–334 (1994).
Von Werner Fischer et al, *Oligosaccharide aus Streptococcus Lactis*, Hoppe–Seyler's Zeitschrift fur Physiologishe Chemie, vol. 350, pp. 1137–1147, Sep. 1969.
Shinkiti Koto et al, α–D–Glucosylation by 6–O–Acetyl–2, 3,4–tri–O–benzyl–D–glucopyranose Using Trimethylsilyl Triflate and Pyridine. Synthesis of α–Maltosyl and α–Isomaltosyl α–D–Glucosides, Bulletin of Chemical Society of Japan, vol. 59, pp. 411–414, Feb. 1986.
Hans Peter Wessel et al, 67, α–D–Glycosyl–Substituted α,α–D–Trehaloses with (1—>4)–Linkage: Syntheses and NMR Investigations, Helvetica Chimica Acta, vol. 74, pp. 682–695, 1991.
Klaus Bock et al, *Carbon–13 Nuclear Magnetic Resonance Data for Oligosaccharides*, Advances in Carbohydrate Chemistry and Biochemistry, vol. 42, pp. 193–225, 1984.
Frank H. Stodola, *The Preparation, Properties and Structure of the Disaccharide Leucrose*, Journal of the American Chemical Society, vol. 78, pp. 2514–2518, Jun. 5, 1956.

*Primary Examiner*—Francisco Prats
*Attorney, Agent, or Firm*—Browdy and Neimark

[57] ABSTRACT

Novel crystalline maltosyl glucoside is obtained by crystallizing maltosyl glucoside from a maltosyl glucoside solution, prepared by exposing either an aqueous solution containing trehalose and an α-glucosyl saccharide or an aqueous solution containing a reducing partial starch hydrolysate to the action of a saccharide-transferring enzyme. The crystalline maltosyl glucoside has non-hygroscopicity, non-reducibility, superior solubility, less fermentability, and other properties of stabilizing oligopeptides and biologically-substances as well as preventing retrogradation of amylaceous substances. These features render it very useful in various compositions including foods, beverages, cosmetics, pharmaceuticals and shaped bodies.

20 Claims, 8 Drawing Sheets

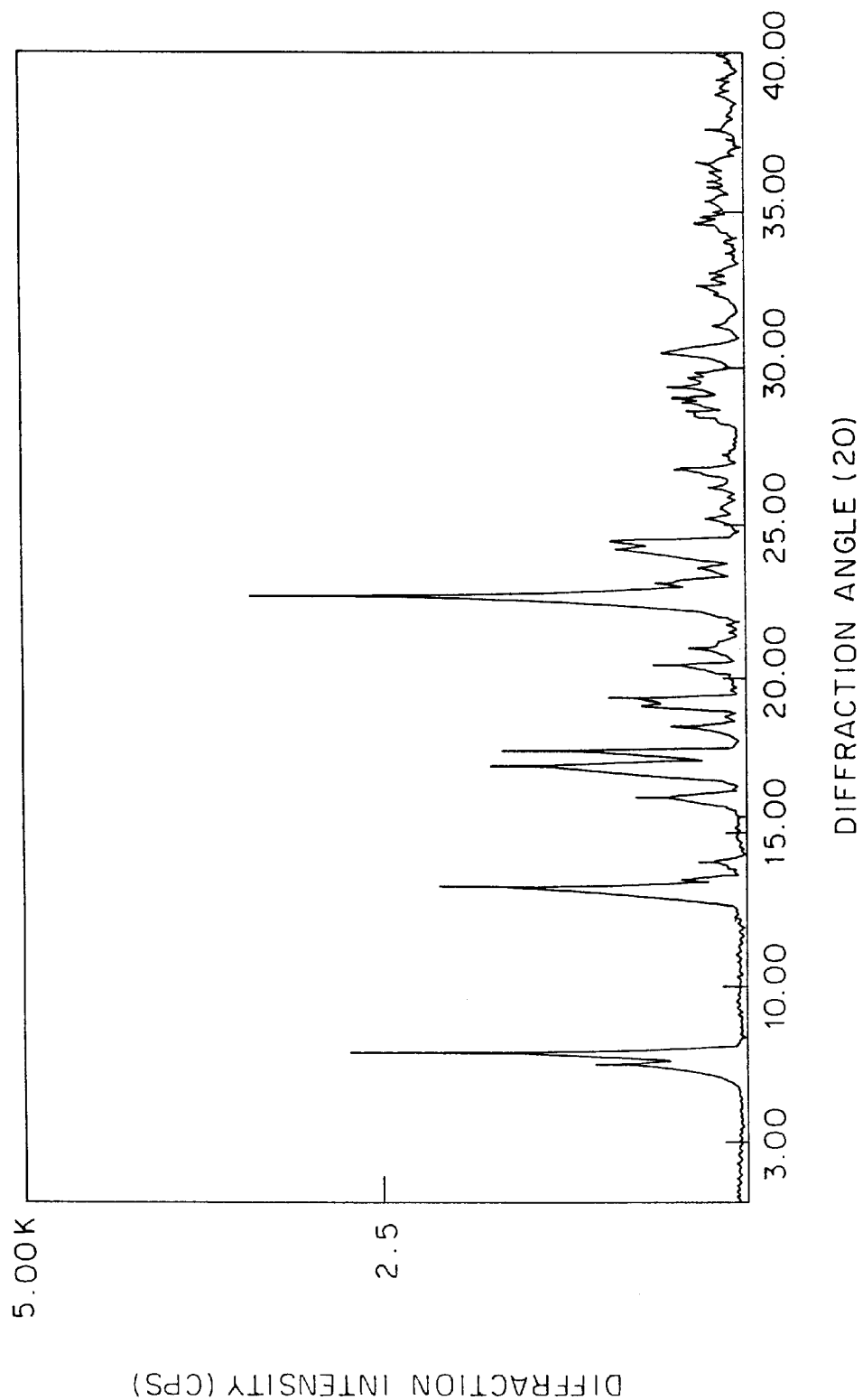

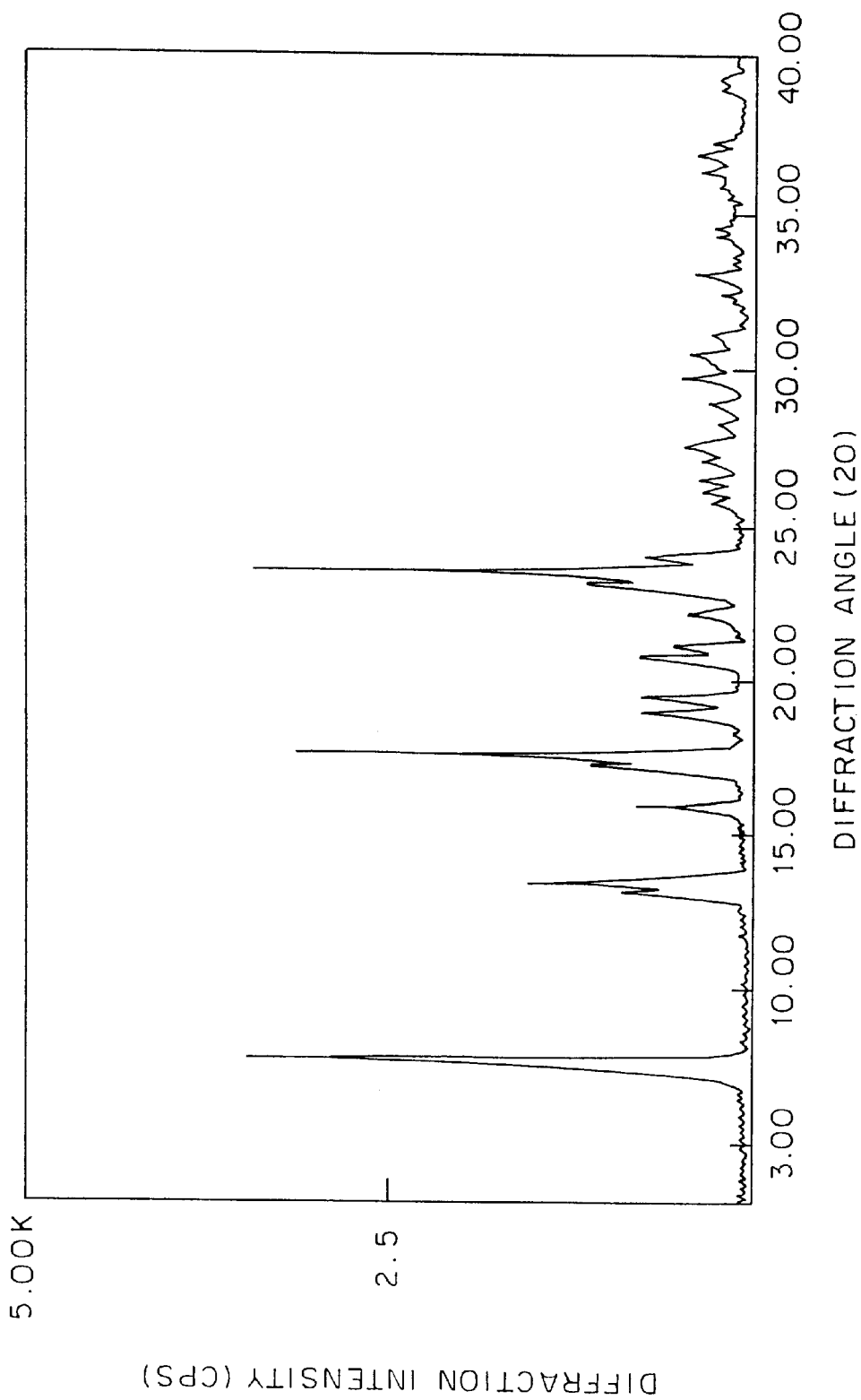

CRYSTALLINE MALTOSYL GLUCOSIDE, AND ITS PRODUCTION AND USE

This application is a continuation of application Ser. No. 08/717,746, filed Sep. 23, 1996, now abandoned, which was a continuation of application Ser. No. 08/396,747, filed Mar. 1, 1995, now abandoned.

BACKGROUND OF THE INVENTION

1. Field of the invention

This invention relates to a novel crystalline saccharide, and its production and use, more particularly, to a crystalline maltosyl glucoside, and its production and use.

2. Description of the prior art

Maltotriose is a tri-saccharide represented by the general formula of O-$\alpha$-D-glucopyranosyl-1$\rightarrow$4)O-$\alpha$-D-glucopyranosyl-(1$\rightarrow$4)D-glucopyranose, and has been known as a sweetener which can be incorporated into syrupy and powdery starch. This saccharide is characteristic of its low sweetness and used in compositions including beverages, foods and tastable products such as tobaccos and cigarettes.

Since maltotriose is a reducing saccharide, it has the drawbacks that it readily causes browning reaction along with proteins and amino acids contained in beverages and foods to readily induce the deterioration and degeneration of these products, and therefore the present inventors have studied means to overcome the drawbacks and found that the preparation of a non-reducing maltosyl glucoside from maltotriose is attained by exposing a reducing partial starch hydrolysate having a glucose polymerization degree of 3 or higher to the action of an enzyme capable of forming a non-reducing saccharide having a trehalose structure as an end unit (hereinafter called "a non-reducing saccharide-forming enzyme" in the present specification), those disclosed in Japanese Patent Application No. 349,216/93, however, the powdery non-reducing saccharide of maltosyl glucoside is amorphous and physically unstable, and, for the sake of stability, the establishment of a more stable crystalline maltosyl glucoside is expected.

On the other hand, as to maltosyl glucoside, for instance, conventional preparation methods as reported by Von Werner Fisher et al. in "*Hoppe-Seyler's Zeitshrift fur Physiologishe Chemie*", Vol.350, pp.1137–1147 (1969), methods for extracting from microorganisms, or in chemical synthetic methods as reported by Shinkiti Koto et al. in "*Bulletin of Chemical Society of Japan*", Vol.59, pp.411–414 (1986) as well as by Hans Peter Wessel et al. in "Helvetica Chimica Acta", Vol.74, pp.682–695 (1991), however, there is no report of and has been unknown a crystallization method for obtaining maltosyl glucoside.

SUMMARY OF THE INVENTION

This invention is to establish a novel crystalline maltosyl glucoside having non-hygroscopicity, non-reducibility, superior free-flowing ability, less fermentability and superior solubility, and to provide its production and use.

To overcome the aforementioned object, this inventors have energetically studied. As a result, they found that maltopentaose, a reducing partial starch hydrolysate, is transformed into a non-reducing maltotetraosyl glucoside by exposing to the action of a non-reducing saccharide-forming enzyme and succeedingly the resultant non-reducing maltotetraosyl glucoside is exposed to the action of $\beta$-amylase to obtain a solution containing maltosyl glucoside and the solution of maltosyl glucoside is applied to a column chromatograph using a strongly-acidic cation exchanger and the resultant solution which contains maltosyl glucoside in a relatively-high content is further concentrated and allowed to stand in a cold-storage room to form a crystal. Furthermore, by clarifying that the resultant crystal is a crystalline maltosyl glucoside, this invention established a novel crystalline maltosyl glucoside, and its production and use. In addition, by clarifying the existence of a hydrous and anhydrous crystalline maltosyl glucoside, this invention accomplished the production of crystals of maltosyl glucosides and their uses.

BRIEF EXPLANATION OF THE ACCOMPANYING DRAWINGS

FIG. 7 illustrates the powder X-ray diffraction figure of hydrous crystalline maltosyl glucoside.

FIG. 8 illustrates the powder X-ray diffraction figure of anhydrous crystalline maltosyl glucoside.

DETAILED DESCRIPTION OF THE INVENTION

Figure 1:
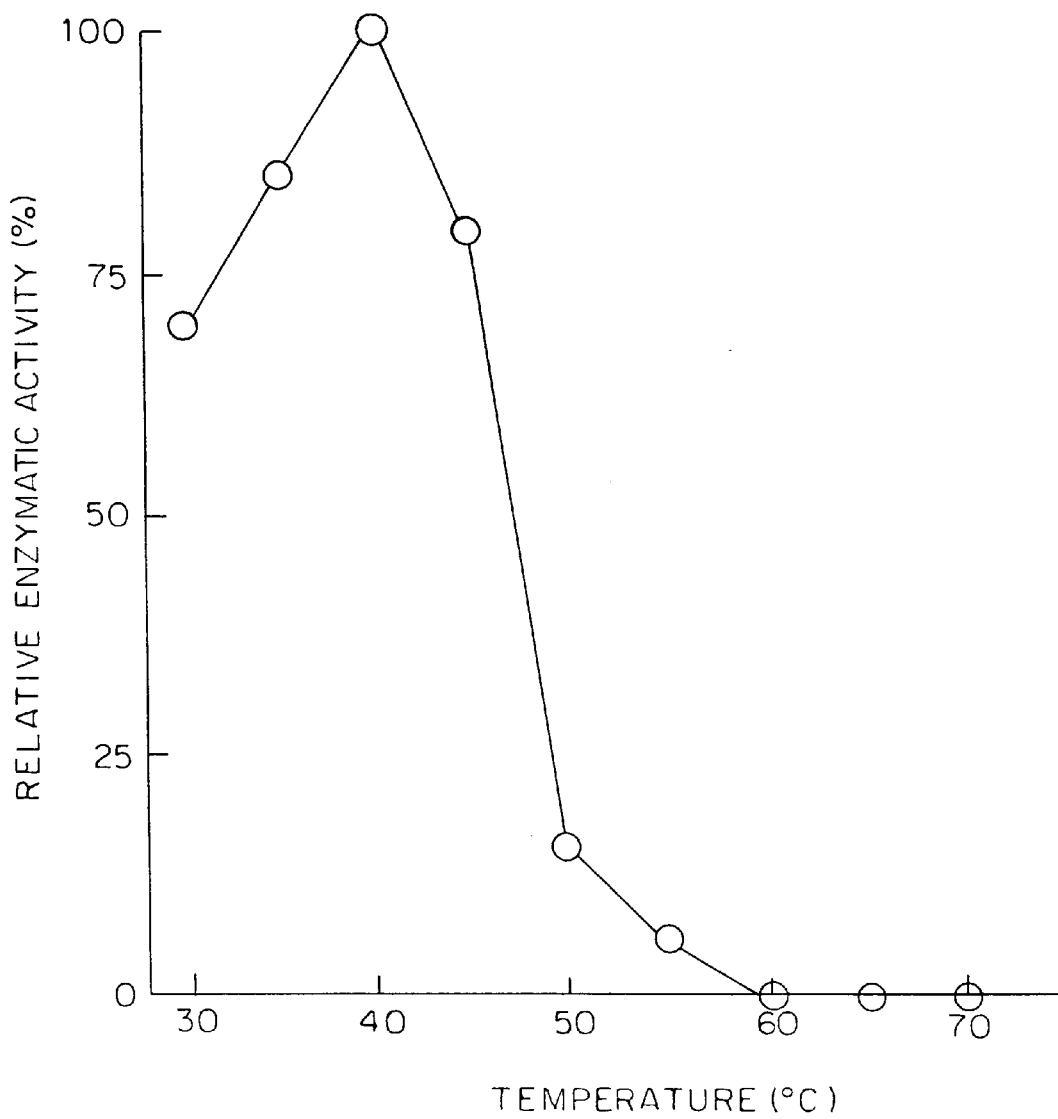
FIG. 1 illustrates the effect of temperature on the activity of non-reducing saccharide-forming enzyme from Rhizobium M-11.

Methods for preparing a crystalline maltosyl glucoside feasible in this invention are those capable of forming the crystal of this invention, usually, crystallizing an aqueous solution of maltosyl glucoside and collecting the resultant crystal.

Methods for preparing a maltosyl glucoside feasible in this invention are chemical methods, generally, biochemical ones wherein a saccharide-transferring enzyme or a non-reducing saccharide-forming enzyme is used.

As a method of using a saccharide-transferring enzyme, for instance, it is feasible in this invention to produce $\alpha$-D-oligoglucosyl glucoside such as maltosyl glucoside, maltotriosyl glucoside and maltotetraosyl glucoside by exposing a solution containing trehalose and $\alpha$-glucosyl saccharide to the action of the saccharide-transferring enzyme, if necessary, the contents of maltosyl glucoside can be arbitrarily elevated by exposing further a solution containing trehalose and $\alpha$-glucosyl saccharide to the action of $\beta$-amylase or the action of a starch-debranching enzyme such as pullulanase or isoamylase together with $\beta$-amylase.

In such a case, $\alpha$-glycosyl saccharides usable in this invention are those wherein one or more glucose residues can be transferred to trehalose via the $\alpha$-1,4 linkage by using a saccharide-transferring enzyme, for example, one or more members selected from the group of starch product, gelatinized starch, liquefied starch, solubilized starch, amylose, amylopectin, reducing partial starch hydrolysate, saccharide-transferred starch product, cyclodextrin, dextrin, maltooligosaccharide and sucrose can be arbitrarily used.

In case that cyclomaltodextrin glucanotransferase (EC 2.4.1.19) or α-amylase (EC 3.2.1.1) is used as a saccharide-transferring enzyme, for example, starch product, gelatinized starch, amylopectin, amylose, reducing partial starch hydrolysate, cyclodextrin, dextrin and maltooligosaccharide can be used preferably, or in the use of α-glucosidase, oligosaccharides such as maltose, maltotriose, maltotetraose and maltopentaose, dextrin and sucrose can be used preferably.

In case that a maltosyl glucoside is prepared by allowing a non-reducing saccharide-forming enzyme to act on a high-purity maltosyl glucoside, usually, a non-reducing saccharide-forming enzyme can be allowed to act on a reducing partial starch hydrolysate having a glucose polymerization degree of 3 or higher to form a non-reducing saccharide having a trehalose structure as an end unit, for example, α-D-oligoglucosyl glucoside such as maltosyl glucoside, maltotriosyl glucoside or maltotetraosyl glucoside. In such a method, if necessary, the contents of maltosyl glucoside can be arbitrarily elevated by allowing β-amylase or a starch-debranching enzyme to act on together with β-amylase, similarly to the case of using a saccharide-transferring enzyme.

The reducing partial starch hydrolysates usable in this invention are those wherein, in the action of a non-reducing saccharide-forming enzyme, maltosyl glucoside or saccharides having the structure of maltosyl glucoside can be formed, usually, starch product, gelatinized starch, liquefied starch, solubilized starch, amylopectin, amylose, dextrin, reducing partial starch hydrolysate with a DE of 1–40 and maltooligosaccharide with a glucose polymerization degree of 3 or higher can be used favorably.

The non-reducing saccharide-forming enzymes usable in this invention are, for example, those disclosed in Japan Patent Application No.349216/93 by this inventors, Rhizobium sp. M-11 and Arthrobacter sp. Q36 which have been deposited in the Patent Microorganism Depository, National Institute of Bioscience and Human-technology, Agency of Industrial Science and Technology, 1–3 Higashi 1-chome, Tsukuba-shi, Ibaraki-ken, Japan, under the accession numbers of FERM BP-4130 and FERM BP-4316 respectively, and enzyme preparations obtainable by cultivating in nutrient culture media conventional microorganisms which are capable of forming non-reducing saccharides, for example, *Brevibacterium helovolum* (ATCC 11822), *Flavobacterium aguatile* (IFO 3772), *Micrococcus luteus* (IFO 3064), *Micrococcus roseus* (ATCC 186), *Curtobacterium citrem* (IFO 15231), *Mycobacterium smegmatis* (ATCC 19420) and *Terrabacter tumescens* (IFO 12960), if necessary, such an enzyme preparation can be purified arbitrarily according to conventional methods prior to use.

The non-reducing saccharide enzymes thus obtained are those which a non-reducing saccharide having a trehalose structure as an end unit when exposed to one or more members selected from the group of reducing partial starch hydrolysates having a glucose polymerization degree of 3 or more.

Any enzymatic reaction conditions can be employed in this invention as long as the enzymatic reaction proceeds, generally, a substrate concentration in the range of 1 to 50 w/w % (the percentages as used hereinafter shall mean "w/w % on a dry solid basis" unless specified otherwise), a temperature in the range of 20 to 80° C., a pH in the range of 4 to 10 and a reaction time in the range of 1 to 100 hours can be used in this invention. The enzymes for such reaction, if necessary, can be used arbitrarily in continuous or batch-wise manner when immobilized by conventional methods including carrier-binding methods, cross-linking methods and entrapping methods.

An aqueous solution obtained by aforementioned enzymatic reaction, usually, contains about 1 to 67% of maltosyl glucoside, and for producing a crystalline maltosyl glucoside from such a solution, generally, impurities are removed from a crude solution and the resultant solution is purified to a highly concentrated solution of maltosyl glucoside, further concentrated and followed by crystallizing maltosyl glucoside, and the resultant crystal is recovered.

As the aforementioned separation and purification, for example, yeast fermentation, membrane filtration, fractional sedimentation, alkali treatment and/or column chromatography can be used arbitrarily. In particular, column chromatography using a strongly-acidic cation exchanger as disclosed in Japan Patent Kokai No.23,799/83 and No.148,794/84 is favorably usable for removing concomitant saccharides and collecting fractions which are rich in maltosyl glucoside. In such a chromatography, conventional fixed-bed method, moving bed method and simulated moving bed method can be used arbitrarily.

For crystallizing maltosyl glucoside from fractions which are rich in maltosyl glucoside, appropriate conditions for a crystallization are chosen depending on the sort of a crystalline form. The conditions for crystallization feasible in this invention are those wherein supersaturated solutions of maltosyl glucoside can be crystallized so as to form maltosyl glucoside, regardless of the method used to produce maltosyl glucoside intact.

In particular, under the aforementioned conditions for crystallization, not less than 60% of maltosyl glucoside solution is concentrated to give a concentration of about 65 to 95% or more, and a temperature of the resultant solution lies in the range wherein the solution is not frozen and not more than the melting point of a crystalline maltosyl glucoside and also there is less possibility of causing the browning reaction and decomposition of maltosyl glucoside, for example, as for a hydrous crystalline maltosyl glucoside, the crystallization of maltosyl glucoside solutions having not less than about 10% water content is feasible at about 10 to 90° C., and as for an anhydrous crystalline maltosyl glucoside, the crystallization of maltosyl glucoside solutions having not more than about 10% water content is feasible in this invention. Additionally, an anhydrous crystalline maltosyl glucoside can be readily produced by drying a hydrous crystalline maltosyl glucoside under reduced pressure or drying on heat. In the process of such a crystallization, ethanol, methanol and/or acetone can be added arbitrarily to the maltosyl glucoside solutions for arranging their supersaturation and viscosity.

The methods for crystallizing maltosyl glucoside according to this invention are those wherein a supersaturated solution containing maltosyl glucoside is adjusted to a relatively-high temperature, placed in a crystallizer and admixed with a seed crystal, desirably, in an amount of 0.1 to 20% and the resultant mixture is cooled gradually while stirring so as to form a massecuite.

A crystalline maltosyl glucoside from the crystallized massecuite is produced in accordance with conventional methods capable of obtaining a crystalline maltosyl glucoside, for example, the conventional separation, block pulverization, fluidized-bed granulation and spray-drying.

For example, separation methods are usually those wherein the crystals of maltosyl glucoside can be separated from molasses by a basket-type centrifuge, if necessary, the resultant crystals can be readily washed by spraying thereto a small amount of chilled water, and such separation methods are suitable for the production of a high-purity crystalline maltosyl glucoside. Others are those wherein there is no process to separate molasses, however, the yield of the production of crystalline maltosyl glucoside can be elevated characteristically although the purity of the resultant crystals is not improved. Accordingly, in this invention, usually, in addition to the crystals of maltosyl glucoside, the crystals obtained contain amylaceous saccharides including trehalose, glucose, maltose, maltotriose and maltotetraose which are present in raw materials or formed in the process of production.

In the spray-drying, usually, massecuite of maltosyl glucoside having a crystallinity of about 25 to 60% is sprayed from a high-pressurized pump through its nozzle, heat-dried at a high temperature that prevents the melting of maltosyl glucoside crystalline powder, for example, at about 60 to 100° C., and aged by blowing thereto a hot air to form a substantially non or less hygroscopic powder of hydrous crystalline maltosyl glucoside.

In the block pulverization, usually, massecuite of maltosyl glucoside having a crystallinity of about 10 to 60% is allowed to stand for 0.5 to 5 days for crystallization so as to form a block. The resultant block is subjected to pulverization or scraping and followed by drying to form a substantially non or less hygroscopic powder of hydrous crystalline maltosyl glucoside On the other hand, the solutions containing maltosyl glucoside is concentrated to give a concentration of not more than 5% water content by heating in accordance with conventional manners so as to obtain a supersaturation solution containing maltosyl glucoside. The resultant solution is admixed with a seed crystal, stirred at a temperature of less than the meting point of crystals of maltosyl glucoside, and shaped into various forms, for example, powder, granule, short rod, plate or cube, and then a substantially non or less hygroscopic hydrous crystal of maltosyl glucoside can be produced favorably.

The crystalline maltosyl glucoside thus obtained is substantially non-hygroscopic and free-flowing although such non hygroscopicity has some variance, and further readily handleable with less viscosity and solidification, and these properties can reduce the material and personnel costs necessary for controlling the package, transportation and storage of crystalline maltosyl glucoside.

The crystalline maltosyl glucoside of this invention is substantially a non or less hygroscopic powder having a relatively high heat-resistance and stability. Such a powder is usable as a vehicle, filler, excipient and powder base for a powdered sweetener mixture, chocolate, chewing gum, instant juice, instant soup, granule and tablet which are obtainable by conventional manners, for example, favorably usable for beverages, cosmetics, pharmaceuticals, shaped bodies and other compositions, and additionally in various applications such as reagents and raw material utilizable in chemical industry.

Furthermore, physicochemical properties of the crystalline maltosyl glucoside such as melting point and specific rotatory power are varied dependently on the purity of the crystalline maltosyl glucoside. The melting point is lowered depending on the decrease of the purity and also its range is widened. For example, the melting point of crystalline maltosyl glucoside having 88.6% purity lies in the range of 138 to 146° C., and therefore a crystalline maltosyl glucoside having purity selected arbitrarily for ceratin usage is obtainable.

Additionally, the crystalline maltosyl glucoside of this invention is readily soluble in water and has a good sweetness. When orally administered, the crystalline maltosyl glucoside is digestible and utilizable as an energy source. Furthermore, since the crystalline maltosyl glucoside is substantially less fermentable by dental caries-inducing microorganisms, it can be used as a cariostatic sweetener, and also since the crystalline maltosyl glucoside has a good sweetness and usefulness as a vehicle, it is favorably usable as a sugar-coating agent of tablets by using together with binders such as pullulan and/or hydroxyethyl starch. In addition, the crystalline maltosyl glucoside has other properties such as body-imparting ability, gloss-imparting ability, moisture-retaining ability, viscosity-imparting ability, heat-resistant ability, acid-resistant ability, and non or low reducibility.

These properties of the crystalline maltosyl glucoside are favorably usable in the production of foodstuffs including foods, beverages, feeds and pet foods as well as in the production of various compositions including cosmetics, pharmaceuticals and shaped bodies.

The crystalline maltosyl glucoside of this invention is usable intact as sweetening seasonings. If necessary, such a crystalline maltosyl glucoside can be used together with an appropriate amount of one or more other sweeteners, for example, powdered starch syrup, glucose, maltose, sucrose, isomerized sugar, honey, maple sugar, sorbitol, dihydrochalcone, stevioside, α-glycosyl stevioside, rebaudioside, glycyrrhizin, L-aspartyl-L-phenylalanine methyl ester, saccharin, glycine and alanine, if necessary, as well as with a filler such as dextrin, starch and lactose.

In addition, powdered crystalline maltosyl glucoside is usable intact as a filler, vehicle or powdering agent, or if necessary, after mixing with other filler, vehicle and/or binder, the crystalline powder can be shaped into a granule, globe, short rod, plate, cube or tablet form arbitrarily because the powder is substantially less hygroscopic, highly heat-resistant and highly stable. Such a powder is favorably usable, for example, as materials for confectioneries and bakery products wherein flour, corn grits and starch are partially or wholly replaced with such a powder.

Further the crystalline maltosyl glucoside of this invention is favorably usable for sweetening foods and beverages in general as well as improving their tastes and qualities because its taste well harmonizes with substances having other types of tastes such as sour, salty, astringent, delicious and bitter tastes, and since the crystalline maltosyl glucoside of this invention is highly acid- and heat-resistant, for example, it is favorably usable as various seasonings including soy sauce, soy sauce powder, miso, miso powder, "moromi (unrefined soy sauce)", "hishio (miso sauce mixed with salted vegetables)", "furikake (fish or laver flour)", mayonnaise, dressing, vinegar, "sanbai-zu (sauce mixing sake, soy and vinegar)". "funmatsu-sushi-su (powdered vinegar for sushi)", "chuka-no-moto (Chinese taste seasoning)", "tentsuyu (soup for tenpura)", "mentsuyu (soup for Japanese-style noodles)", sauce, ketchup, "yakiniku-no-tare (soup for grilled meat)", curry roux, stew premix, soup premix, "dashi-no-moto (dried bonito taste seasoning)", mixed seasoning, "mirin (heavily sweetened sake)", "shin-mirin (synthetic mirin)", table sugar and coffee sugar. In addition, the crystalline maltosyl glucoside of this invention is favorably usable to sweeten, for example, Japanese-style confectioneries such as "senbei (rice crackers)", "arare (glutinous rice crackers)", "okoshi (millet and rice crackers)", rice cake, "manju (bun with a bean-jam filling)", "uiro (sweet rice jelly)", "an (bean jam)", "yokan (sweet jelly of beans)", "mizu-yokan (soft adzuki-bean jelly)", kingyoku", jelly, castellan and "amedama (Japanese-style toffee)"; Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as those for fruit preserve and "kaki-gori (shaved ice)"; spreads and pastes such as flour paste, peanut paste and fruit paste; processed fruits and vegetables such as jam, marmalade, syrup-preserved fruit and crystallized fruit; pickled products such as "fukujin-zuke (sliced vegetables pickled in soy sauce)", "bettara-zuke (fresh radish pickles)", "senmai-zuke" and "rakkyo-zuke (pickled shallots)"; premixes for pickled products such as "takuan-zuke-no-moto" and "hakusai-zuke-no-moto"; meat products such as ham and sausage; fish meat products such as fish meat ham, fish meat sausage, "kamaboko (boiled fish paste)", "chikuwa (bamboo wheels shaped kamaboko)" and "tenpura (deep fried foods)"; relishes such as "uni-no-shiokara (salted guts of sea urchin)", "ika-no-shiokara (salted guts of squid)", "sukonbu", "saki-surume" and "fugu-no-mirinboshi"; "tsukudani (food boiled down in soy sauce)" such as those of "nori (dried seaweed)", "sansai (mountain vegetables)", "surume (dried squid)", small fish and shellfish; daily dishes such as "nimame (cooked beans)", potato salad and "konbu-maki (tangle roll)"; milk products; bottled and canned products such as those of meat, fish meat, fruit and vegetable; alcoholic drinks such as synthetic sake, liqueur, wine and whisky; beverages such as coffee, tea, cocoa, juice, carbonated beverage, lactic acid beverage and lactobacillus beverage; premixes and instant foodstuffs such as pudding premix, hot cake premix, "sokuseki-shiruko (premix of adzuki-bean soup with rice cake)" and instant soup; baby foods; diet foodstuffs; and nutrient beverage, as well as to improve their tastes and qualities.

Further the crystalline maltosyl glucoside of this inventican can be used in feeds and pet foods for domestic animals and poultry including honey bee, silkworm and fish so as to improve their taste qualities. The crystalline maltosyl glucoside of this invention is favorably usable as a sweetener for orally-usable products in the form of a solid, paste or liquid including cosmetics and pharmaceuticals such as a tobacco, cigarette, dentifrice, lipstick, lip cream, internal medicine, troche, codliver oil drop, oral refreshing agent, cachou and gargle, in addition, usable as a taste quality improver and taste masking agent.

The crystalline maltosyl glucoside according to this invention is favorably utilizable as a stabilizer, osmosis-controlling agent, vehicle, moisture-controlling agent, viscosity-controlling agent and quality-improving agent in the production of cosmetics, for example, soap, skin cream, body shampoo, hair cream, lip cream, skin refining agent and hair restorer.

The crystalline maltosyl glucoside of this invention is also favorably usable in the production of pharmaceuticals as a stabilizer for activities of biologically-active substance or active ingredients in such a substance, for example, cytokines including interferon-α, interferon-β, interferon-γ, tumor necrosis factor-α, tumor necrosis factor-β, macrophage-migration inhibitory factor, colony stimulating factor, transfer factor and interleukin 2; hormones such as insulin, growth hormone, prolactin, erythropoietin and follicle-stimulating hormone; vaccines such as BCG vaccine, Japanese encephalitis vaccine, measles vaccine, poliomyelitis vaccine, vaccinia virus vaccine, tetanus toxoid, *Antivenenum Trimeresurus flavoviridis* and human immunoglobulin; antibiotics such as penicillin, erythromycin, chloramphenicol, tetracycline, streptomycin and kanamycin sulfate; vitamins such as thiamine, riboflavin, L-ascorbic acid, cod-liver oil, carotenoid, ergosterol and tocopherol; enzymes such as lipase, elastase, urokinase, protease and glucanase; extracts such as ginseng extract, snapping turtle extract, chlorella extract, propolis extract and royal jelly; and viable microorganisms such as virus, lactobacillus, bifid bacteria and yeast. In addition, the crystalline maltosyl glucoside of this invention is usable as an osmosis-controlling agent, vehicle, intubation feeding, sugar coating agent and syrup agent in the production of pharmaceuticals. To incorporate the crystalline maltosyl glucoside of this invention in the compositions including foods, beverages, cosmetics, pharmaceuticals and shaped bodies, conventional methods, for example, mixing, kneading, dissolving, melting, soaking, permeating, spreading, applying, coating, spraying, injecting and solidifying are arbitrarily used before completion of their processing. The amount of the crystalline maltosyl glucoside to be incorporated is, usually, 0.1% or more, desirably, 0.5% or more in products, dependently on the compositions containing the crystalline maltosyl glucoside. The compositions thus obtained can be extensively used in foods, beverages, cosmetics and pharmaceuticals which are perorally or parenterally used, as well as in domestic, agricultural, forestry, fishery and chemical industrial products.

The following experiments will explain this invention in detail.

Experiment A explains the preparation, purification and characterization of a non-reducing saccharide-forming enzyme from Rhizobium M-11, and then illustrates the preparation of trehalose and non-reducing saccharides with a trehalose structure as an end unit from reducing partial starch hydrolysates by using such an enzyme. Experiment B explains the preparation and physicochemical properties of the crystalline maltosyl glucoside of this invention.

Experiment A-1

Production of non-reducing saccharide-forming enzyme in Rhizobium M-11

A liquid culture medium consisting of 2.0 w/v % maltose, 0.5 w/v % peptone, 0.1 w/v % yeast extract, 0.1 w/v % disodium hydrogen phosphate, 0.1 w/v % potassium dihydrogen phosphate and water was adjusted to pH 7.0. The liquid medium was divided into 100 ml aliquots which were then placed separately in 500 ml-flasks, sterilized at 120° C. for 20 minutes, cooled, inoculated with Rhizobium M-11 (FERM BP-4130) and incubated at 27° C. for 24 hours under stirring condition of 130 rpm, thus obtaining a seed culture.

About 20 liters of a culture medium which had the same composition as used in the seed culture was allocated in 30 1-jar fermenter, sterilized, cooled to 30° C., inoculated with 1 v/v % of the seed culture and incubated at 30° C. and pH 6.0–8.0 for 24 hours under aeration and agitation conditions. The enzymatic activity of the resultant culture was about 1.5 units/ml. A portion of the culture was centrifugally separated into cells and supernatant and the former cells were then suspended in 50 mM phosphate buffer (ph 7.0) to give the starting volume, and followed by assaying the resultant cell suspension and supernatant for enzymatic activity. As the result, in the cell suspension about 0.6 units/ml of enzymatic activity was found, while about 0.9 units/ml of enzymatic activity was found in the supernatant.

The non-reducing saccharide-forming enzyme is assayed as follows: To 4 ml of 1.25 w/v % maltopentaose as a substrate (50 mM phosphate buffer, pH 7.0) is added 1ml of an enzyme solution and the mixture is incubated at 40° C. for 60 minutes, heated at 100° C. for 10 minutes to inactivate the enzyme, correctly diluted by a factor of 10 in deionized water and determined for reducing power by the Somogyi-Nelson method. As a control, a fresh preparation of the same enzyme solution is inactivated by heating at 100° C. for 10 minutes and then tested similarly as above. One unit activity of the enzyme is defined as the amount of enzyme that diminishes 1 micromole of reducing power in terms of the amount of maltopentaose per minute under the above conditions.

Experiment A-2

Purification of enzyme

About 18 liters of the culture obtained in Experiment A-1 was treated with "MINI-LAB", a super-high pressure cell homogenizer (a product of Dainippon Pharmaceutical Co., Ltd., Osaka, Japan) to crush cells. The resultant was centrifuged at 10,000 rpm for 30 minutes to obtain about 16 liters of supernatant. In the supernatant was dissolved ammonium sulfate to give a saturation degree of 0.2 and the resultant was allowed to stand at 4° C. for 1 hour and then centrifuged at 10,000 rpm for 30 minutes to obtain a supernatant.

Additionally, in the supernatant was dissolved ammonium sulfate to give a saturation degree of 0.6 and the resultant was allowed to stand at 4° C. for 24 hours and then centrifuged at 10,000 rpm for 30 minutes to collect the resultant sediment. The sediment was dissolved in 10mM phosphate buffer (pH 7.0), dialyzed against a fresh preparation of the same buffer for 24 hours and centrifuged at 10,000 rpm for 30 minutes to remove insoluble substances. The dialyzed solution (360 ml) was divided into two portions which were then separately applied to ion-exchange column chromatography using 300 ml "DEAE TOYOPEARL®" gel of Tosoh Corporation, Tokyo, Japan.

The objective enzyme having adsorbed on the gel was eluted from the column with a fresh preparation of the same phosphate buffer containing sodium chloride. The obtained enzyme-active fractions were dialyzed against a fresh preparation of the same phosphate buffer containing 2M ammonium sulfate and further centrifuged at 10,000 rpm for 30 minutes to remove insoluble substances, and the resultant supernatant was applied to hydrophobic column chromatography using 300 ml "BUTYL TOYOPEARL® 650", a gel of Tosoh Corporation, Tokyo, Japan. The enzyme having adsorbed on the gel was eluted therefrom with a linear gradient buffer decreasing from 2M to 0M ammonium sulfate, and the enzyme-active fractions were collected. In addition, the fractions were applied to gel filtration chromatography using 300 ml "TOYOPEARL® HW-55", a gel of Tosoh Corporation, Tokyo, Japan, and the enzyme-active fractions were collected. The enzymatic activity, specific activity and yield in each purification step were tabulated in Table 1.

The purified enzyme preparation thus obtained as an eluate in the gel filtration step in Table 1 was determined for its purity on electrophoresis using polyacrylamide gel (7.5 w/v %) and the electrophoresis gave a single protein band, meaning that the enzyme preparation was electrophoretically homogenous and highly pure.

TABLE 1

| Purification step | Enzyme activity (units) | Specific activity (units/mg protein) | Yield (%) |
| --- | --- | --- | --- |
| Culture | 26,800 | — | 100 |
| Supernatant after cell crushing | 20,300 | 0.10 | 76 |
| Dialyzed solution after salting-out | 16,100 | 0.32 | 60 |
| Eluate from ion-exchange column | 11,300 | 5.5 | 42 |
| Eluate from hydrophobic column | 5,730 | 98.0 | 21 |
| Eluate from gel filtration | 3,890 | 195.0 | 15 |

Experiment A-3

Characterization of enzyme

A portion of the purified enzyme preparation obtained in Experiment A-2 was applied to gel electrophoresis containing 10 w/v % SDS-polyacrylamide and then determined for its molecular weight by comparison with standard molecular markers (a product of Nippon Bio-Rad Laboratories KK, Tokyo, Japan) which had been electrophoresed on a fresh preparation of the same gel, revealing that the molecular weight of the enzyme was about 77,000–87,000 daltons.

Another portion of the purified enzyme preparation was applied to isoelectrophoresis using 2 w/v % "AMPHOLINE", a polyacrylamide gel of Pharmacia LKB, Uppsala, Sweden, and then determined for its isoelectric point by measuring the pH of the electrophoresed gel, revealing that the isoelectric point of the enzyme was about 3.6–4.6.

Figure 2:
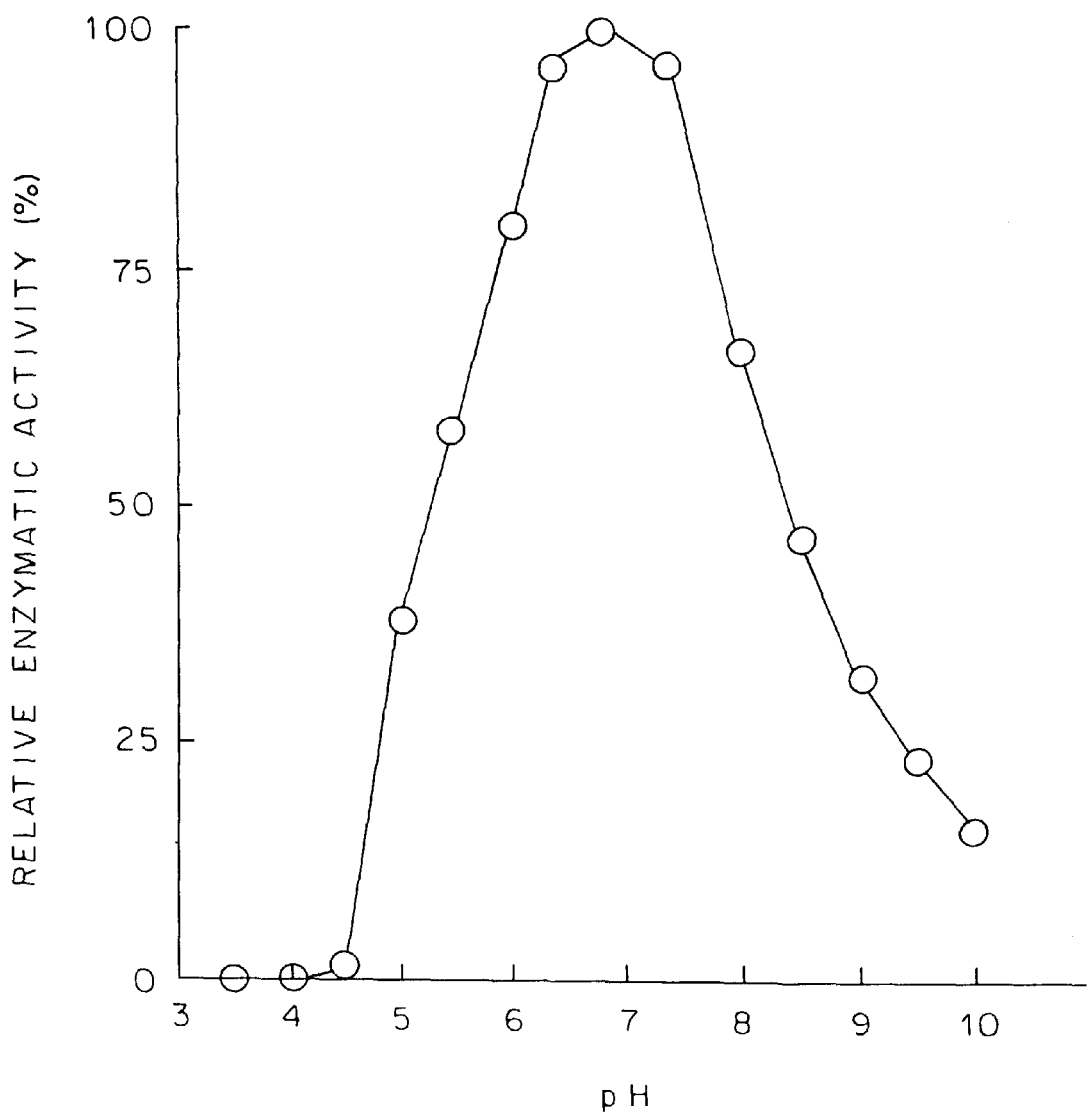
FIG. 2 illustrates the effect of pH on the activity of non-reducing saccharide-forming enzyme from Rhizobium M-11.
Figure 3:
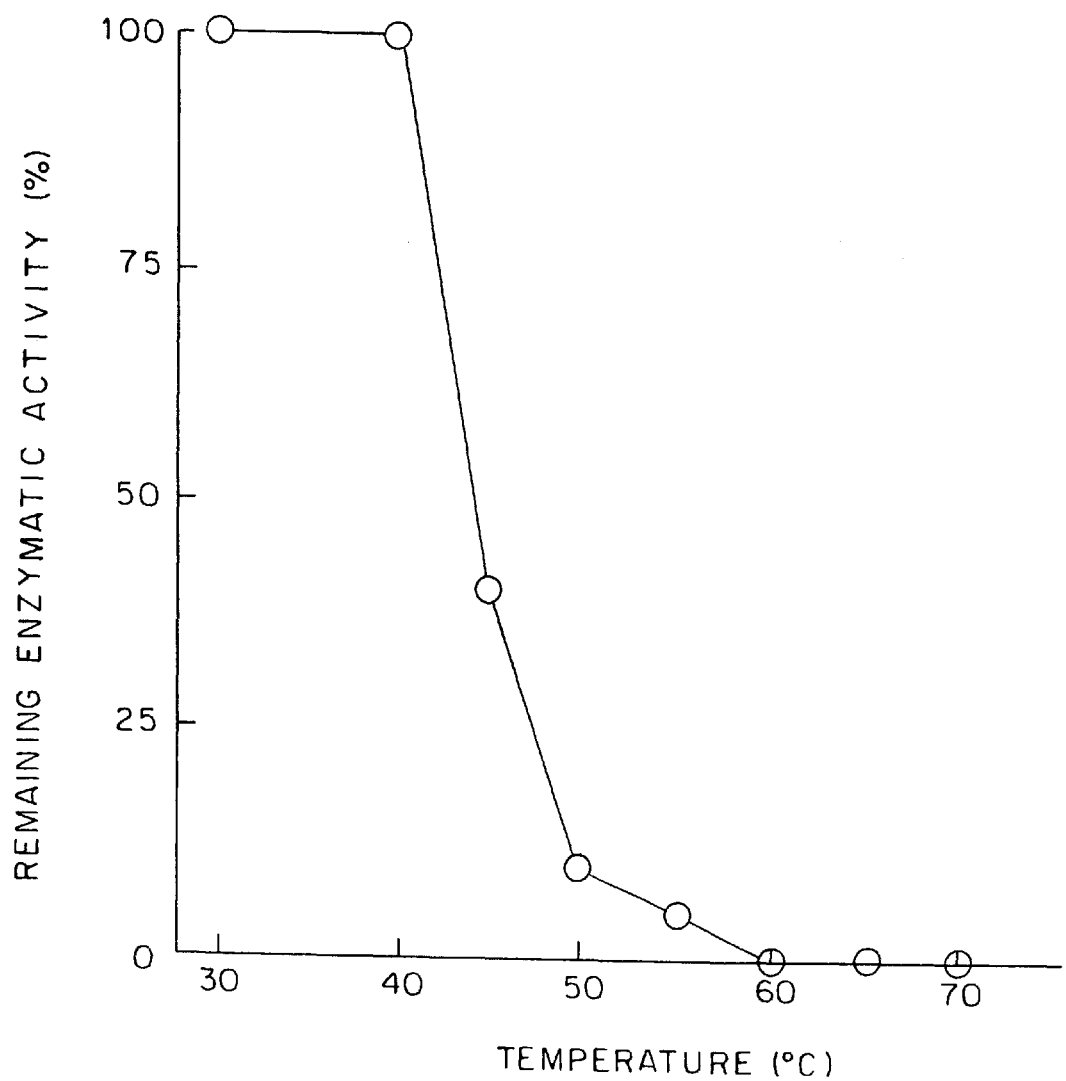
FIG. 3 illustrates the thermal stability of non-reducing saccharide-forming enzyme from Rhizobium M-11.
Figure 4:
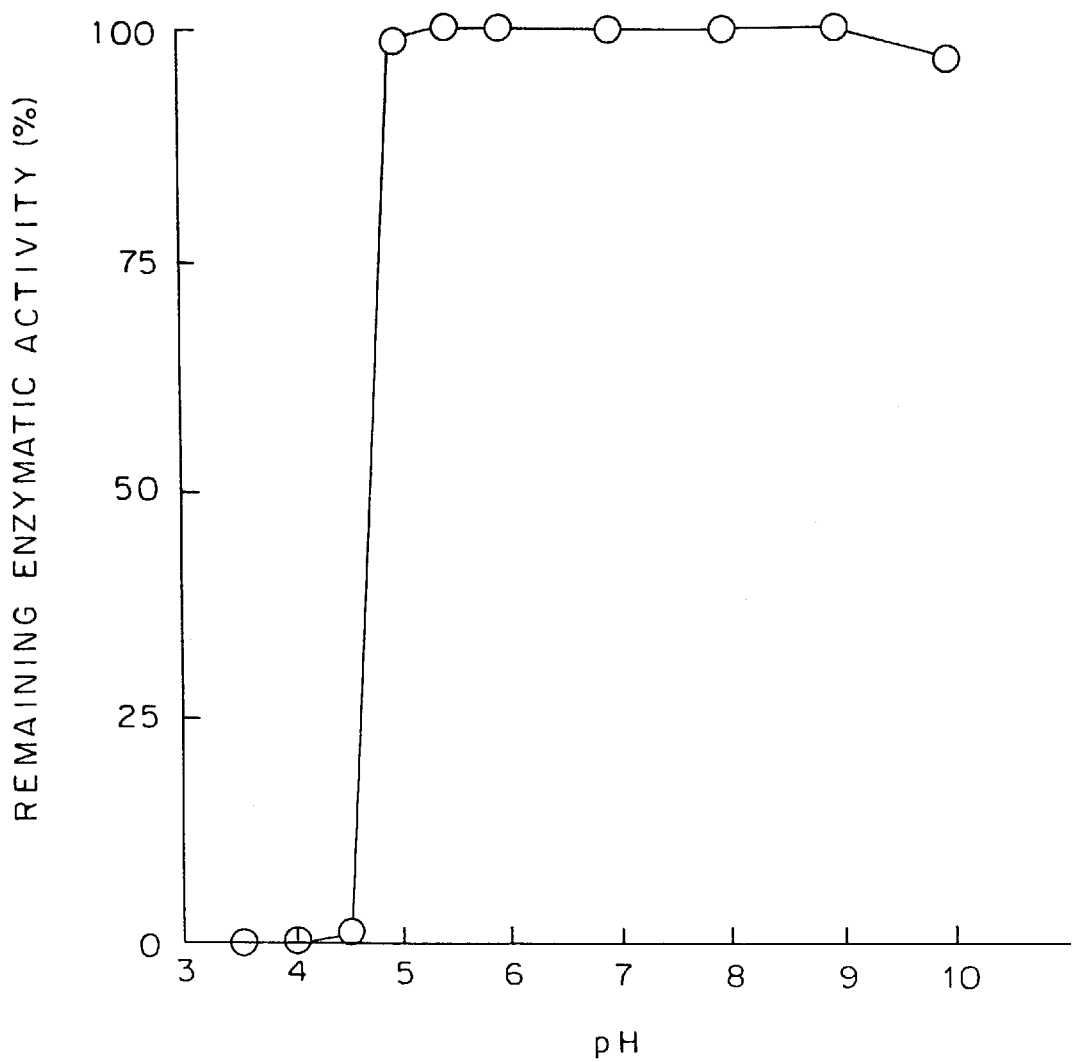
FIG. 4 illustrates the pH stability of non-reducing saccharide-forming enzyme from Rhizobium M-11.

Effects of temperature and pH on the enzymatic activity were tested in accordance with the aforementioned assay method. The results were respectively as shown in FIGS. 1 and 2. The optimum temperature was found to be around 40° C. when incubated at pH 7.0 for 60 minutes, while the optimum pH was about 7.0 when incubated at 40° C. for 60 minutes. Thermal stability of the enzyme was determined by incubating it in 50 mM phosphate buffer, pH 7.0, at different temperatures for 60 minutes, cooling in water bath and assaying the residual enzymatic activity. While the pH stability was determined by incubating the enzyme in 50 mM phosphate buffers at different pHs and 25° C. for 16 hours, adjusting the buffers to pH 7.0 and assaying the residual activities. The results were respectively as shown in FIGS. 3 (thermal stability) and 4. The enzyme was stable at a temperature up to 40° C. and at a pH in the range of about 6–9.

Experiment A-4

Preparation of non-reducing saccharide

Aqueous solutions containing 20 w/v % of either glucose, maltose, maltotriose, maltotetraose, maltopentaose, maltohexaose or maltoheptaose as a substrate were admixed with 2 units/g substrate, d.s.b., of the purified enzyme standard obtained in Experiment A-2 and reacted at 40° C. and pH 7.0 for 48 hours and the resultants were deionized and analyzed for reaction products on high-performance liquid chromatography (HPLC) using "WAKOBEADS WB-T-330" column (a product of Wako Pure Chemical Industries, Ltd., Osaka, Japan). The high-performance liquid chromatography was carried out at ambient temperature, and water as an eluent was applied to the column at a flow rate of 0.5 ml/minute while monitoring the eluate with "RI-8012", a differential refractometer (a product of Tosoh Corporation, Tokyo, Japan). The results were as shown in Table 2.

TABLE 2

| Substrate | Reaction product | Elution Time on HPLC (minutes) | Composition (%) |
|---|---|---|---|
| Glucose | Glucose | 33.4 | 100.0 |
| Maltose | Maltose | 28.5 | 100.0 |
| Maltotriose | PI | 23.3 | 35.0 |
|  | Maltotriose | 25.9 | 65.0 |
| Maltotetraose | PII | 21.6 | 85.6 |
|  | Maltotetraose | 24.1 | 14.4 |
| Maltopentaose | PIII | 19.7 | 92.7 |
|  | Maltopentaose | 22.6 | 7.3 |
| Maltohexaose | PIV | 18.7 | 93.5 |
|  | Maltohexaose | 21.4 | 6.5 |
| Maltoheptaose | PV | 17.8 | 93.4 |
|  | Maltoheptaose | 21.0 | 6.6 |

Note: PI, PII, PIII, PIV and PV in the Table designate the newly formed products from respective substrates, i.e. maltotriose, maltotetraose, maltopentaose, maltohexaose and maltoheptaose.

As evident from the results in Table 2, the reaction products consisted of residual substrates and newly formed saccharides PI, PII, PIII, PIV and PV and no other saccharides were substantially detected. The yields for PI having a glucose polymerization degree of 3 was relatively low, however, that for PII, PIII, PIV and PV, which had a glucose polymerization degree of 4 or higher, were high, i.e. 85% or higher. It was revealed that no saccharide was formed from glucose and maltose.

For purifying these newly formed saccharides, the reaction products were decolored, deionized, concentrated and subjected to column fractionation using a strongly-acidic cation exchanger in alkali-metal form ("XT-1016", $Na^+$form, 4% cross-linking degree, a product of Tokyo Organic Chemical Industries, Ltd., Tokyo, Japan). More particularly, the cation exchanger was packed in 3 jacketed stainless steel columns, inner diameter of 2.0 cm, length of 1 m each, cascaded in series, which were then loaded with either reaction product in an amount of 5 v/v % to the volume of the cation exchanger and then applied with 55° C. water at an SV (space velocity) 0.13 for fractionation, and fractions containing 97% or more newly formed saccharides were collected. The obtained fractions were separately lyophilized into high-purity saccharide preparations. The yields against particular material substrates were about 9% for PI, about 65% for PII, about 82% for PIII, about 80% for PIV and about 77% for PV, and the final purities were 97.5% for PI, 98.6% for PII, 99.5% for PIII, 98.4% for PIV and 98.4% for PV.

These high-purity saccharide preparations were tested for their reducing powers with the Somogyi-Nelson method and their reducing powers were represented in terms of DE (dextrose equivalent). The results were given in Table 3.

TABLE 3

| Saccharide preparation | Purity (%) | DE |
|---|---|---|
| PI | 97.5 | 0.83 |
| PII | 98.6 | 0.35 |
| PIII | 99.5 | 0.10 |
| PIV | 98.4 | 0.27 |
| PV | 98.4 | 0.23 |

As evident from the results in Table 3, all the preparations exhibited only a slight reducing power. It was suggested that the reducing power would be due to a trace amount of reducing maltooligosaccharides from the substrates which had been remained in the preparations, as well as that all the newly formed saccharides were substantially free from reducing power.

Experiment A-5
Enzymatic degradation using glucoamylase

Fifty milligrams of either non-reducing saccharide preparation PI, PII, PIII, PIV or PV obtained in Experiment A-4 was dissolved in 1ml of 50 mM acetate buffer (pH 4.5) and the resultant solutions were mixed with 1 unit of glucoamylase (a product of Seikagaku Corporation, Tokyo, Japan), incubated at 40° C. for 6 hours for enzymatic degradation and analyzed for degraded products on HPLC. As a result, only glucose and trehalose were detected in all the degraded products. The contents and molar ratios of glucose and trehalose were as shown in Table 4.

TABLE 4

| Saccharide preparation | Glucose (%) | Trehalose (%) | Molar ratio (glucose/trehalose) |
|---|---|---|---|
| PI | 36.2 | 63.8 | 1.07 |
| PII | 52.0 | 48.0 | 2.06 |
| PIII | 61.4 | 38.6 | 3.02 |
| PIV | 68.3 | 31.7 | 4.09 |
| PV | 72.9 | 27.1 | 5.11 |

As evident from the results in Table 4, it was revealed that PI was degraded by glucoamylase into 1 glucose molecule and 1 trehalose molecule; PII, into 2 glucose molecules and 1 trehalose molecule; PIII, into 3 glucose molecules and 1 trehalose molecule; PIV, into 4 glucose molecules and 1 trehalose molecule; and PV, into 5 glucose molecules and 1 trehalose molecule.

Considering the reaction characteristics of glucoamylase, these saccharide preparation would have a structure where one or more glucose molecules are bound to trehalose molecule via the $\alpha$-1,4 or $\alpha$-1,6 linkage: In particular, PI is a non-reducing saccharide with a glucose polymerization degree of 3 where 1 glucose molecule is bound to 1 trehalose molecule; PII, a non-reducing saccharide with a glucose polymerization degree of 4 where 2 glucose molecules are bound to 1 trehalose molecule; PIII, a non-reducing saccharide with a glucose polymerization degree of 5 where 3 glucose molecules are bound to 1 trehalose molecule; PIV, a non-reducing saccharide with a glucose polymerization degree of 6 where 4 glucose molecules are bound to 1 trehalose molecule; and PV, a non-reducing saccharide with a glucose polymerization degree of 7 where 5 glucose molecules are bound to 1 trehalose molecule. It was revealed that after exposing PI, PII, PIII, PIV and PV to $\beta$-amylase, PI and PII were not hydrolyzed, but PIII was hydrolyzed into 1 maltose molecule and one PI molecule; PIV, into 1 maltose molecule and 1 PII molecule; and PV, into 2 maltose molecules and one PI molecule.

The above results suggest that the reaction by the non-reducing saccharide-forming enzyme according to this invention would be an intramolecular conversion reaction which does not accompany neither degradation nor polymerization of substrates, in other words, it does not change their glucose polymerization degrees. Thus PI, PII, PIII, PIV and PV produced by the enzyme would be $\alpha$-glucosyl trehalose (as represented by Gn-T where G and T represent glucose residue and $\alpha,\alpha$-trehalose respectively, while n is an integer of 1 or more), more particularly, $\alpha$-glucosyl trehalose (or $\alpha$-maltosyl glucoside), $\alpha$-maltosyl trehalose (or $\alpha$-maltotriosyl glucoside), $\alpha$-maltotriosyl trehalose (or $\alpha$-maltotetraosyl glucoside), $\alpha$-maltotetraosyl trehalose (or α-maltopentaosyl glucoside) and α-maltopentaosyl trehalose (or α-maltohexaosyl glucoside) respectively.

Experiment A-6

Preparation of trehalose and non-reducing saccharide having trehalose structure as an end unit Forty parts by weight of a partial starch hydrolysate ("PINE-DEX #4", a product of Matsutani Chemical Ind., Co., Ltd., Kyoto, Japan) was dissolved in 60 parts by weight of water while heating, and the resultant solution was heated to 45° C., adjusted to pH 6.5, mixed with 1 unit/g reducing partial starch hydrolysate of a non-reducing saccharide-forming enzyme prepared by the method in Experiment A-2, and reacted for 96 hours to form non-reducing saccharides having a trehalose structure as an end unit, followed by heating the resultant at 100° C. for 10 minutes to inactivate the enzyme. The reaction mixture was then diluted to about 20%, admixed with 10 units/g partial starch hydrolysate of "Glucozyme", a glucoamylase product or specimen of Nagase Biochemicals Ltd., Kyoto, Japan, reacted for 40 hours and heated to inactivate the enzyme. The resultant solution was decolored with activated carbon, deionized with ion-exchanger and concentrated into about 60% solution in usual manner. The obtained saccharide solution contained 29.5% trehalose. This concentrate was then charged to a stainless steel column prepacked with a strongly-acidic cation exchanger ("CG6000", Na$^+$ form, a product of Japan Organo, Co., Ltd., Tokyo, Japan) at 60° C. and an SV 0.4, and fractions rich in trehalose were collected. The fractions contained about 90% trehalose. The fractions were then concentrated to about 75%, fed to a crystallizer, mixed with about 2% crystalline trehalose hydrate as a seed crystal and gradually cooled to obtain a massecuite which had a crystallinity of about 45%. The massecuite was then sprayed from a nozzle equipped on the upper part of a drying tower at a pressure of 150 kg/cm$^2$. At the same time, 85° C. air was sent from the upper part of the drying tower towards its bottom, and the resultant powder, which had been accumulated on a wire netting of a conveyer provided at the bottom of the drying tower, was gradually conveyed out of the drying tower while sending thereto 45° C. air through under the wire netting. Thereafter the crystalline powder was fed to an aging tower and aged in a stream of hot air for 10 hours to complete its crystallization and dehydration, thus obtaining crystalline trehalose hydrate powder.

Experiment B-1

Preparation of maltosyl glucoside

Five parts by weight of 98% maltopentaose (a product of Hayashibara Biochemical Laboratories, Inc., Okayama, Japan) were dissolved in 10 parts by weight of water while heating, and the resultant solution was heated to 40° C. and adjusted to pH 7.0, admixed with a non-reducing saccharide-forming enzyme prepared by the method in Experiment A-2 in an amount of 2 units/g maltopentaose, and then reacted for 48 hours, followed by heating the reaction mixture at 100° C. for 20 minutes to inactivate the enzyme. The resultant solution contained about 88% maltotetraosyl glucoside.

The aforementioned solution containing maltotetraosyl glucoside was heated to 40° C., adjusted to pH 5.5, admixed with "#1500", β-amylase (a product of Nagase Biochemicals Ltd., Kyoto, Japan) in an amount of 20 units/g partial starch hydrolysate, d.s.b., reacted for 24 hours and succeedingly heated at 100° C. for 20 minutes to inactivate the enzyme. The resultant solution contained about 53% maltosyl glucoside along with maltose and maltotriose.

The solution thus obtained was in usual manner decolored with an activated charcoal, desalted with an ion-exchange resin (H$^+$ or OH$^-$ form) and concentrated to give a concentration of about 50%, and according to the methods in Experiment A-6, the solution thus concentrated was charged to a column prepacked with a strongly-acidic cation exchange resin, followed by collecting fractions rich in maltosyl glucoside. The fractions were pooled into a solution containing about 81% maltosyl glucoside.

For further elevating the purity, the solution was admixed with sodium hydroxide up to 0.1N and heated at 100° C. for 2 hours to decompose reducing saccharides. The solution thus reacted was in usual manner decolored, desalted and concentrated to give a concentration of about 50%. The concentrated solution contained about 94% maltosyl glucoside, and further applied to a preparative liquid chromatography prepacked with "YMC-PACK R-355-15", an octadecyl silica gel (a product of YMC Co., Ltd., Kyoto, Japan) as a column for preparative liquid chromatography, and fractions containing maltosyl glucoside in an amount of about 99% or higher were collected.

The above fractions, according to usual manners, were purified and concentrated to give a concentration of 78%, and the fractions thus concentrated were allocated in a beaker, followed by standing it in 40° C. cool room to form a crystal. The crystal was centrifuged and washed by spraying thereto a small amount of water to obtain 99.9% hydrous crystalline product. The product was dried under a reduced pressure at 100° C. overnight to obtain an anhydrous crystalline product.

These crystalline products were determined for their physicochemical properties and the results were as follows.

(1) Elemental analysis (as anhydride)

Hydrous crystal C=42.4%, H=6.8%

Anhydrous crystal C=42.6%, H=6.7%

Theoretical value C=42.86%, H=6.39%

(2) Mass spectrum analysis (as anhydride)

MW=504 (for molecular formula: $C_{18}H_{32}O_{16}$)

(3) Water content

Measured by the Karl Fischer's method

Hydrous crystal 9.9% (molar ratio of maltosyl glucoside to water =1:3)

Anhydrous crystal 0.3%

(4) Melting point

Added hydrous or anhydrous crystal of maltosyl glucoside to a melting point apparatus was observed its melting point under an elevating temperature rate of 1° C. per minute. Both crystals were melted at 180° C. The result does not necessary mean that such melting points of both crystals are the same because, for example, it could be considered that hydrous crystal was converted into an anhydrous crystal without changing its appearance while heating at an elevating temperature and that the melting of the anhydrous crystal was only observed.

(5) Specific rotatory power (as anhydride)

Both hydrous- and anhydrous-crystals had the following specific rotatory power.

$[\alpha]_D^{20}$+207.9° (c=5.0, H$_2$O)

(6) Ultraviolet absorption spectrum

Both hydrous and anhydrous crystals exhibited no characteristic absorption spectra, when analyzed in their aqueous solutions.

(7) Infrared absorption spectrum

Figure 5:
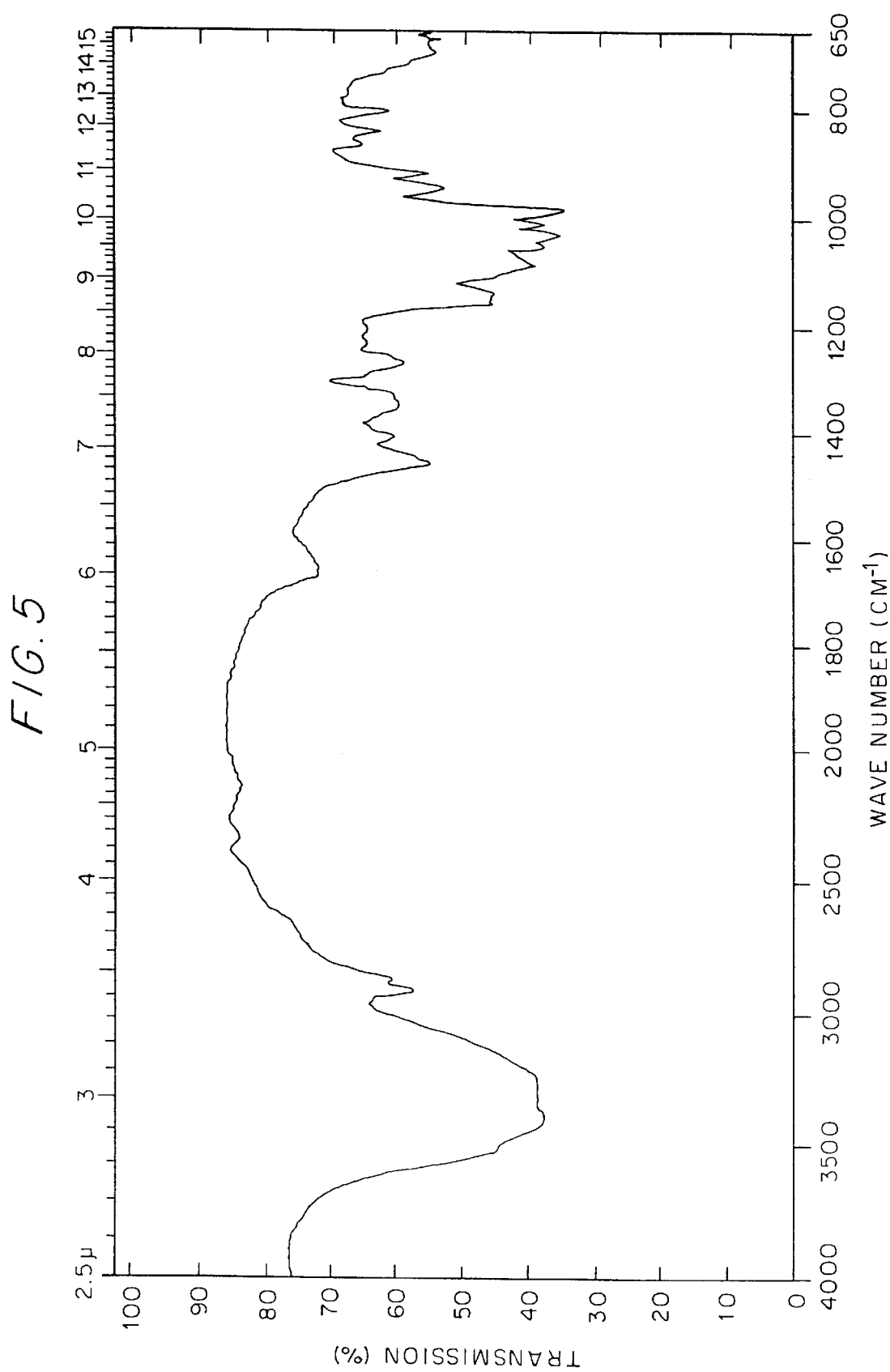
FIG. 5 illustrates the infrared absorption spectrum of hydrous crystalline maltosyl glucoside.

Two milligrams of powdered hydrous or anhydrous crystal and 200 mg of dried KBr were mixed and prepared into a transparent tablet which was then analyzed for infrared absorption spectrum. As the results, the crystals exhibited almost the same pattern of infrared absorption spectrum. The result of hydrous crystal was as shown in FIG. 5.

(8) Solubility (as anhydride)

Up to about 163 g each hydrous and anhydrous crystals were respectively soluble in 100 ml of 25° C. water.

(9) Sweetness (as anhydride)

The sweetness of 25% of aqueous solution of maltosyl glucoside was equivalent to that of 10% aqueous sucrose solution. The crystals of this invention had about 40% sweetening power of sucrose, and the quality of such a sweetness is very satisfactory.

(10) Coloring reaction

The hydrous and anhydrous crystals were colored green by the anthrone-sulfuric acid reaction but were negative to both the Fehling's reaction and iodine reaction.

(11) Structure (as anhydride)

(a) Upon hydrolysis by IN sulfuric acid, the crystals formed D-glucose only.

(b) When exposed to glucoamylase, the crystals each formed one mole of glucose and of neotrehalose.

Figure 6:
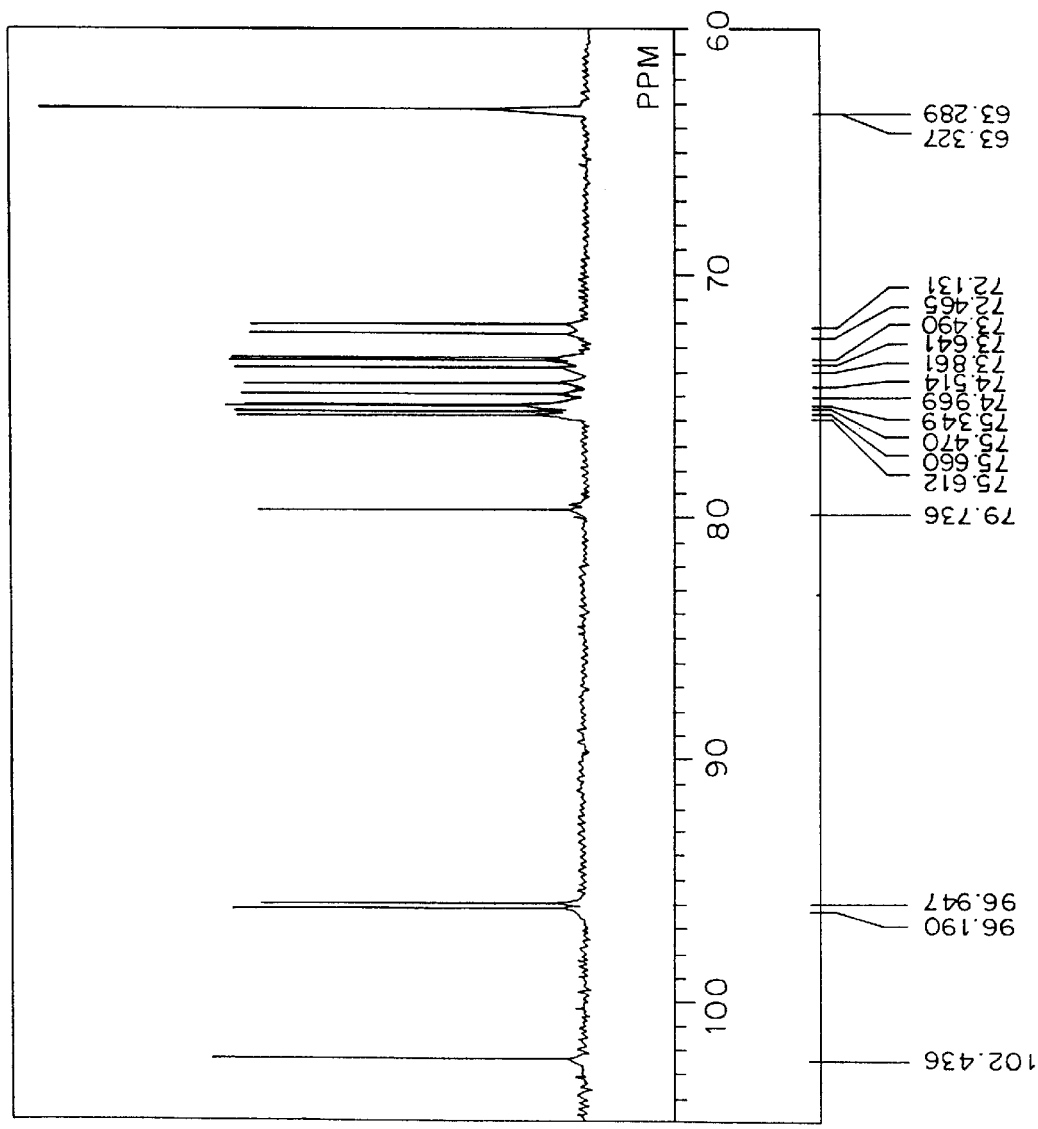
FIG. 6 illustrates the results of carbon nuclear resonance analysis of maltosyl glucoside.

(c) The result on carbon nuclear resonance analysis was as shown in FIG. 6. All the carbon atoms of the crystals were assigned to the chemical shifts of α-D-glucopyranose, α,α-trehalose and maltooligosaccharide as standard substances reported by Klaus Bock et al., in *Advances in Carbohydrate Chemistry and Biochemistry*, Vol.42, pp.192–225 (1984), and it was suggested that the crystals had a structure represented by O-α-D-glucopyranosyl-(→4)-α-D-glucopyranosyl α-D-glucopyranoside, that is maltosyl glucoside.

(12) Powder X-ray diffraction Crystalline maltosyl glucoside was determined for powder x-ray diffraction figure using CuKα-ray in accordance with the method reported by F.H. Stodola et at., in *Journal of the American Chemical Society*, Vol.78, pp.2,514–2,518 (1956). The result of hydrous crystal or anhydrous crystal was as shown in FIG. 7 or FIG. 8 respectively. As evident from the results in FIG. 7 and FIG. 8, hydrous crystal gave predominant diffraction angles (2θ) of 7.9°, 13.2°, 17.2° and 22.8°, while anhydrous crystal gave predominant diffraction angles of 7.7°, 13.5°, 17.6° and 23.6° on powder x-ray diffraction analysis.

Based on the above results, the crystals of the present invention can be acknowledged as the crystals of maltosyl glucoside which have been unknown.

Experiment B-2

Hygroscopicity of crystalline maltosyl glucoside and amorphous crystalline maltosyl glucoside, and its effects About 1 g powder of hydrous crystalline maltosyl glucoside, anhydrous crystalline maltosyl glucoside or amorphous crystalline maltosyl glucoside was placed in a polyethylene vessel and allowed to stand in high humidity conditions of 90.1% relative humidity, and the changes of moisture content and appearance of these powders were observed and measured at a prescribed interval. Hydrous and anhydrous crystals, which were prepared by the methods of Experiment B-1, and amorphous crystal, which was prepared by dissolving hydrous crystal substance in deionized water and dried in vacuo to obtain a test sample. The results were shown in Table 5.

As evident from the results in Table 5, amorphous crystalline maltosyl glucoside was very hygroscopic, readily solidified, and free flowing. On the other hand, hydrous crystal was less hygroscopic, free flowing, and readily handleable, while anhydrous crystal was hygroscopic, however, had no change of appearance and retained free-flowing ability, therefore it was considered that anhydrous crystal was converted into hydrous crystal and stabilized.

TABLE 5

|  | Time period (hour) | | | |
| --- | --- | --- | --- | --- |
|  | 0 | 2 | 8 | 24 |
| Hydrous crystal | 9.9 | 10.4 | 10.5 | 10.5 |
| Water content(%) | ++ | ++ | ++ | ++ |
| Appearance |  |  |  |  |
| Anhydrous crystal | 0.3 | 10.3 | 10.4 | 10.5 |
| Water content(%) | ++ | ++ | ++ | ++ |
| Appearance |  |  |  |  |
| Amorphous crystal | 0.5 | 6.3 | 17.4 | 20.0 |
| Water content(%) | ++ | + | – | – |
| Appearance |  |  |  |  |

Note: The symbols "++", "+" and "–" mean powdery and free flowing, slightly solidified but free flowing, and solidified into syrup and losing free-flowing appearance, respectively.

Experiment B-3

Acute toxicity

Hydrous and anhydrous crystalline maltosyl glucosides prepared by the method in Experiment B-1 were tested for acute toxicity in mice upon oral administration. As a result, the crystalline maltosyl glucosides were found to be low intoxity, and no mouse died even when administered the maximum administrable dose. These suggest that their $LD_{50}$ would be briefly 50 g/kg or higher.

The following Examples A and B illustrate the production of the present crystalline maltosyl glucoside and uses of the same respectively:

EXAMPLE A-1

Fifty parts by weight of 95% maltopentaose, a product commercialized by Hayashibara Biochemical Laboratories, Inc., Okayama, Japan, was dissolved in 200 parts by weight of water while heating and the resultant solution was adjusted to 40° C. and pH 7.0, admixed with a non-reducing saccharide-forming enzyme prepared by the method in Experiment A-2 in an amount of 5 units/g maltopentaose, reacted for 24 hours, followed by heating to inactivate the enzyme. Thereafter the solution contained 83% maltotetraosyl glucoside. The solution was concentrated to give about 50% concentration, d.s.b., allowed to stand in a chilled room to form crystals of maltosyl glucoside, followed by filtration to obtain a crystalline maltosyl glucoside.

Ten parts by weight of the present crystalline maltosyl glucoside was dissolved in 100 parts by weight of water while heating, and the resultant solution was heated to 50° C. and adjusted pH 5.5, admixed with 20 units/g solid of "β-amylase #1500" commercialized by Nagase Biochemicals Ltd., Kyoto, Japan, reacted for 24 hours and heated for 20 minutes at 100° C. to inactivate the enzyme. The solution contained 58% maltosyl glucoside and small amounts of maltose and maltotriose.

The solution was decolored with activated charcoal, desalted with ion-exchange resin ($H^+$ and $OH^-$ form) and concentrated in the usual manner to give about 50% concentration, d.s.b. This concentrate was then charged to a jacketed stainless steel column (cascaded 4 columns, 5.4 cm×4 m) prepacked with a strongly-acidic cation exchange (cascaded 4 columns, 5.4 cm×4 m)("XT-1016", $Na^+$ form, a product of Japan Organo, Co., Tokyo, Japan) at 60° C. and SV 0.4, and eluted with 60° C. water to collect fractions which were rich in maltosyl glucoside. The fractions were pooled and the solution contained about 92% maltosyl glucoside.

The solution was decolored with activated carbon, desalted with ion-exchange resin (H$^+$ and OH$^-$ form) and concentrated in usual manner to give about 80% concentration, d.s.b., and placed in a crystallizer and admixed with 2% crystalline maltosyl glucoside as a seed crystal, and the resultant mixture was cooled gradually while stirring for crystallization to form a massecuite. The massecuite thus obtained was separated from molasses by a basket-type centrifuge, washed by spraying thereto a small amount of water, followed by drying the resultant to obtain about 99.4% hydrous crystalline maltosyl glucoside.

The product thus obtained exhibits substantially no hygroscopicity and is readily handleable, and it is favorably useful in a variety of compositions including foods, beverages, cosmetics, pharmaceuticals and shaped bodies as a sweetener, taste improver, quality improver, stabilizer and vehicle.

EXAMPLE A-2

About 20% potato starch containing 0.1% calcium carbonate was adjusted to pH 6.0, and then admixed with "Termamyl 60L", α-amylase commercialized by Novo Nordisk Bioindustry, Copenhagen, Denmark, in an amount of 0.3% with respect to starch solid, liquefied at 95–100° C. and heated to inactivate the enzyme, thus a liquefied starch solution with DE 19.5 was obtained.

The resultant solution was heated to 40° C. and adjusted to pH 6.2, admixed with a non-reducing saccharide-forming enzyme prepared by the method in Experiment A-2 in an amount of 3 units/g starch together with isoamylase commercialized by Hayashibara Biochemical Laboratories, Inc., Okayama, Japan, in an amount of 1000 units, and reacted for 72 hours. The mixed solution was heated to inactivate the enzymes, and then cooled to 50° C. and adjusted to pH 5.5. The resultant solution was admixed with 50 units/g solid of "β-amylase #1500" commercialized by Nagase Biochemicals Ltd., Kyoto, Japan, reacted for 24 hours and heated to inactivate the enzyme. The solution contained about 21% maltosyl glucoside.

The solution was purified, concentrated and subjected to a column chromatography using a strongly-acidic cation exchange resin in the same way as Example A-1 to obtain fractions which were rich in maltosyl glucoside. The fractions were pooled and the solution contained about 89% maltosyl glucoside.

The solution was decolored with activated charcoal, desalted with ion-exchange resin (H$^+$ and OH$^-$ form) and concentrated in the usual manner to give about 85% concentration, and admixed with 2% crystalline maltosyl glucoside as a seed crystal, and the resultant mixture was cooled gradually while stirring for crystallization. The massecuite thus obtained was separated from molasses by a basket-type centrifuge, washed by spraying a small amount of water, followed by drying the resultant to obtain about 98.1% hydrous crystalline maltosyl glucoside.

The product thus obtained exhibits substantially no hygroscopicity and is readily handleable, and it is favorably useful in a variety of compositions including foods, beverages, cosmetics, pharmaceuticals and shaped bodies as a sweetener, taste improver, quality improver, stabilizer and vehicle.

EXAMPLE A-3

"PINE-DEX #4", a partial starch hydrolysate commercialized by Matsutani Chemical Ind., Co., Ltd., Kyoto, Japan, was adjusted to 20% concentration, 45° C. and pH 5.5, and admixed with 500 units/g partial starch hydrolysate of isoamylase and reacted for 24 hours to decompose the α-1, 6 linkages of starch. The solution thus reacted was heated at 100° C. and allowed to stand for 10 minutes, and then cooled to 40° C. and adjusted to pH 6.5. The resultant solution was admixed with 5 units/g solid of non-reducing saccharide-forming enzyme prepared by the method in Experiment A-2 and reacted for 48 hours, and the solution thus reacted was heated at 100° C., allowed to stand for 10 minutes and cooled. The solution was heated to 50° C., admixed with 50 units/g solid of β-amylase as well as 10 units/g solid of α-amylase, reacted for 24 hours and heated at 100° C. for 20 minutes to inactivate the enzymes. The solution contained about 24% maltosyl glucoside.

The solution was purified, concentrated and subjected to a column chromatography using a strongly-acidic cation exchange resin in the same way as Example A-1 to obtain fractions which were rich in maltosyl glucoside. The fractions contained about 91% maltosyl glucoside.

The fractions were pooled, decolored with activated carbon, desalted with ion-exchange resins (H$^+$ and OH$^-$ form) and concentrated in usual manner to give about 85% concentration, and admixed with 3% crystalline maltosyl glucoside as a seed crystal, and the resultant mixture is crystallized while gradually stirring to obtain a massecuite having about 45% crystallinity.

The massecuite thus obtained was sprayed from a nozzle equipped on the upper part of a drying tower at a pressure of 150 kg/cm$^2$. At the same time, 85° C. air was sent from the upper part of the drying tower towards its bottom and the resultant powder, which had been accumulated on a wire netting of a conveyer provided at the bottom of the drying tower was gradually conveyed out from the drying tower while sending thereto 45° C. air through under the wire netting. Thereafter the crystalline powder was fed to an aging tower and aged in a stream of hot air for 10 hours to complete its crystallization and dehydration, and thus a crystalline maltosyl glucoside powder was obtained.

The product thus obtained, which exhibits substantially no hygroscopicity and is readily handleable, is favorably useful in a variety of compositions including foods, beverages, cosmetics, pharmaceuticals and shaped bodies as a sweetener, taste improver, quality improver, stabilizer and vehicle.

EXAMPLE A-4

The solution highly containing maltosyl glucoside which had been obtained in the same way as in Example A-3 by reacting a partial starch hydrolysate with isoamylase and non-reducing saccharide-forming enzyme and then reacting the resultant solution with β-amylase and α-amylase, followed by the separation and purification and concentrating the resultant to give about 80% concentration. The concentrated solution was allocated to a crystallizer, admixed with 2% crystalline maltosyl glucoside as a seed crystal and crystallized while gradually stirring, and thereafter allocated to a vessel to form a block. The block was allowed to stand at about 25° C. for 2 days, aged, pulverized by a cutting-type pulverizer, dried by a fluidized-bed drying and classified to obtain a hydrous crystalline maltosyl glucoside powder.

The product thus obtained exhibits substantially no hygroscopicity and is readily handleable, and it is favorably useful in a variety of compositions including foods, beverages, cosmetics, pharmaceuticals and shaped bodies as a sweetener, taste improver, quality improver, stabilizer and vehicle.

EXAMPLE A-5

The hydrous crystalline maltosyl glucoside, prepared by the method in Example A-1, was dried at 100° C. under reduced pressure over night to obtain an anhydrous crystalline maltosyl glucoside having about 0.2% water content.

The product, when allowed to stand in a room, adsorbed moisture and was converted into hydrous crystalline maltosyl glucoside having about 10% water content for stabilization. The anhydrous crystalline maltosyl glucoside can be favorably used as a seed crystal, and also useful as a hygroscopic agent, dehydrating agent and chemical raw material, and further utilizable in a variety of compositions including foods, beverages, cosmetics, pharmaceuticals and shaped bodies.

EXAMPLE A-6

One part by weight of trehalose and one part by weight of "PINE-DEX #4", a partial starch hydrolysate commercialized by Matsutani Chemical Ind., Co., Ltd., Kyoto, Japan, were dissolved in 3 parts by weight of water while heating, and the resultant solution was cooled 65° C., adjusted pH 6.0 and admixed with 10 units/g partial starch hydrolysate of a cyclomaltodextrin glucanotransferase derived from *Bacillus stearothermophilus* commercialized by Hayashibara Biochemical Laboratories, Inc., Okayama, Japan, reacted for 24 hours and heated to inactivate the enzyme. Thereafter the solution was adjusted to 55° C., admixed with 25 units/g partial starch hydrolysate of pullulanase commercialized by Hayashibara Biochemical Laboratories, Inc., Okayama, Japan, and 50 units/g partial starch hydrolysate of β-amylase, reacted for 24 hours and heated to inactivate the enzymes. The solution contained about 25% maltosyl glucoside.

The solution was purified and subjected to a column chromatography using a strongly-acidic cation exchange resin in the same way as in Example A-1 to obtain fractions which were rich in maltosyl glucoside. The fractions were pooled, decolored, desalted, concentrated, crystallized and allocated into a vessel to form a block. The block was pulverized, dried and classified to obtain a powder containing a hydrous crystalline maltosyl glucoside in a yield of about 17% against the starting material.

The product thus obtained exhibits substantially no hygroscopicity and is readily handleable, and it is favorably useful in a variety of compositions including foods, beverages, cosmetics, pharmaceuticals and shaped bodies as a sweetener, taste improver, quality improver, stabilizer and vehicle.

EXAMPLE B-1

Sweetener

One part by weight of a high-purity hydrous crystalline maltosyl glucoside obtained by the method in Example A-1 and 0.05 parts by weight of "αG Sweet", α-glycosyl stevioside commercialized by Toyo Sugar Refining Co., Ltd., Tokyo, Japan, were mixed to homogeneity and the mixture was fed to granulator to obtain a granular sweetener. The sweetener has a superior taste quality and about two-fold stronger sweetening power and the calorie in terms of sweetening power is about one half of that of sucrose. The sweetener is suitable as a low-calorie sweetener to sweeten low-calorie foods and beverages for those having obesity or diabetes whose calorie intakes are restricted, and furthermore the sweetener is also suitable to sweeten foods and beverages which are designed to suppress dental caries because it is lower in acid and insoluble glucan production by cariogenic microorganisms.

EXAMPLE B-2

Hard candy

One hundred parts by weight of a 55% sucrose solution and thirty parts by weight of a powder containing hydrous crystalline maltosyl glucoside obtained by the method in Example A-3 were mixed while heating, and the mixture was concentrated to give a moisture content lower than 2% by heating in vacuo, mixed with 1 parts by weight of citric acid and appropriate amounts of lemon flavor and coloring agent and shaped in usual manner. The product is a high-quality hard candy which is crisp, superior in taste quality and free of crystallization of sucrose.

EXAMPLE B-3

Strawberry jam

One hundred and fifty parts by weight of fresh strawberry, 60 parts by weight of sucrose, 20 parts by weight of maltose, 40 parts by weight of a powder containing hydrous crystalline maltosyl glucoside obtained by the method in Example A-4, 5 parts by weight of pectin and 1 part by weight of citric acid were boiled down in a pot and the resultant was bottled. The product is a jam, having a superior flavor and color.

EXAMPLE B-4

Cream wafer

Two thousand parts by weight of a high-purity anhydrous crystalline maltosyl glucoside, 1000 parts by weight of shortening, 1 part by weight of lecithin, 1 part by weight of lemon oil and 1 part by weight of vanilla oil were mixed in usual manner to prepare a cream. The cream was heated to 40–45° C. and put between wafers while keeping at temperature to obtain a cream wafer. The product having a smoothly meltable cream has a superior taste and flavor.

EXAMPLE B-5

Sweetened condensed-milk

Five parts by weight of a high-purity hydrous crystalline maltosyl glucoside obtained by the method in Example A-2 was dissolved in 100 parts by weight of fresh milk, and the resultant solution was sterilized by heating with plate heater, concentrated to about 70% and sterilely canned. The product, having a mild sweetness and superior flavor, is favorably usable in baby foods and seasonings for fruits, coffee, cocoa and tea.

EXAMPLE B-6

Lactic acid beverage

Ten parts by weight of defatted milk was pasteurized at 80° C. for 20 minutes, cooled to 4° C., mixed with 0.3 parts by weight of starter and fermented at 37° C. for 10 hours. The resultant was homogenized, mixed with 5 parts by weight of a high-purity hydrous crystalline maltosyl glucoside obtained by the method in Example A-2 and 2 parts by weight of isomerized sugar and the mixture was pasteurized by keeping it at 70° C. The mixture was cooled, mixed with an appropriate amount of flavoring agent and bottled. The product is a high-quality lactic acid drink having flavor and sweetness which are well harmonized with sour taste.

EXAMPLE B-7

Powdered juice

Thirty three parts by weight of spray-dried orange juice was mixed with 50 parts by weight of a high-purity hydrous crystalline maltosyl glucoside obtained by the method in Example A-2, 10 parts by weight of sucrose, 0.65 parts by weight of citric anhydride, 0.1 part by weight of malic acid, 0.1 part by weight of L-ascorbic acid, 0.1 part by weight of sodium citrate, 0.5 parts by weight of pullulan and an appropriate amount of powdered flavoring agent to homogeneity, pulverized into a fine powder, fed to fluidized-bed granulator and granulated at ventilation temperature of 40° C. for 30 minutes while spraying to the contents as a binder a syrup with a high content of maltosyl glucoside obtained by the method in Example A-2, and divided into a prescribed amount and packaged. The product is a powdered juice which has an about 30% natural fruit juice. The product is free of undesirable taste and smell, hygroscopicity and solidification, and very stable over an extended storage period.

EXAMPLE B-8

Chocolate

Forty parts by weight of cacao paste, 10 parts by weight of cacao butter, 20 parts by weight of sucrose and 30 parts by weight of a high-purity hydrous crystalline maltosyl glucoside obtained by the method in Example A-1 were mixed, and the resultant mixture was fed to a refiner to reduce particle size, fed to a conche and kneaded at 50° C. for 2 days. While such kneading to, the mixture was added 0.5 parts by weight of lecithin, sufficiently mixed and dispersed. Thereafter the mixture was kept at 31° C. with thermo-controller, poured in molds immediately before solidification of the butter, deaerated with vibrator and passed through 10° C. cooling tunnel over 20 minutes to complete solidification. The contents in the molds were then taken out and packaged. The product, having no hygroscopicity, superior color, gloss and texture, has a satisfiable inner texture and smoothly melts in the mouth to exhibit a gentle sweetness and mild flavor.

EXAMPLE B-9

Chewing gum

Three parts by weight of gum base was softened by heating, admixed with 4 parts by weight of "MABIT®", an anhydrous crystalline maltitol commercialized by Hayashibara Shoji, Inc., Okayama, Japan, and 3 parts by weight of high-purity hydrous crystalline maltosyl glucoside obtained by the method in Example A-2, admixed with appropriate amounts of flavoring and coloring agents, kneaded with roller, shaped and packaged in usual manner. The product is a chewing gum having a superior texture, flavor and taste.

EXAMPLE B-10

Custard cream

One hundred parts by weight of corn starch, 100 parts by weight of a powder containing hydrous crystalline maltosyl glucoside obtained by the method in Example A-3, 80 parts by weight of "SUNMALT®" a maltose commercialized by Hayashibara Shoji, Inc., 20 parts by weight of sucrose and one part by weight of sodium chloride were mixed to homogeneity, and the resultant mixture was admixed with 280 parts by weight of fresh egg, mixed by stirring, gradually admixed with 1,000 parts by weight of boiling milk, heated on fire while stirring till the corn starch was gelatinized and the mixture wholly became semi-transparent, cooled, admixed with an appropriate amount of vanilla flavor, divided into prescribed amount and packaged. The product has a smooth gloss, mild sweetness and delicious taste.

EXAMPLE B-11

Uiro-no-moto (instant "uiro")

Ninety parts by weight of rice powder was admixed to homogeneity with 20 parts by weight of corn starch, 120 parts by weight of a powder containing high-purity hydrous crystalline maltosyl glucoside obtained by the method in Example A-6 and 4 parts by weight of pullulan to homogeneity to obtain "uiro-nomo-to". The "uiro-no-moto" was kneaded with appropriate amounts of "maccha" (a green tea powder) and water and the resultant mixture was divided in vessels and steamed for 60 minutes to obtain "maccha-uiro". The product has a smooth gloss, good palatability and delicious taste, and also has a long shelf life because retrogradation of starch is effectively suppressed.

EXAMPLE B-12

Instant corn potage soup

Thirty parts by weight of α-corn powder, 5 parts by weight of α-flour, 4 parts by weight of α-potato starch, 12 parts by weight of α-waxy corn starch, 8 parts by weight of a powder containing hydrous crystalline maltosyl glucoside obtained by the method in Example A-3, 5 parts by weight of glutamic acid sodium, 8.5 parts by weight of sodium chloride, 7 parts by weight of defatted milk powder and 0.5 parts by weight of onion powder were mixed sufficiently, and the mixture was admixed with 0.5 parts by weight of sorbitan fatty acid ester and 9 parts by weight of hardened oil which were dissolved while heating, and further admixed with 10 parts by weight of lactose. The resultant mixture was fed to fluidized-bed granulator, sprayed with a small amount of water and granulated at ventilation temperature of 70° C. by the same way in Example B-7, and divided into a prescribed amount and packaged to obtain an instant corn potage soup. The product is a delicious tasting soup which can be readily dissolved by mixing with hot water.

EXAMPLE B-13

"Bettara-zuke-no-moto"

Four parts by weight of a powder containing hydrous crystalline maltosyl glucoside prepared by the method in Example A-4, 0.05 parts by weight of licorice powder, 0.008 parts by weight of malic acid, 0.07 parts by weight of sodium glutamate, 0.03 parts by weight of potassium sorbate and 0.2 parts by weight of pullulan were mixed to homogeneity to obtain "bettara-zuke-no-moto", a premix for preparing fresh radish pickles. Thirty kilograms of fresh radish were soaked in sodium chloride in the usual manner and thereafter soaked in sucrose, and the radish thus prepared was soaked in the solution prepared with 4 kg of the "bettara-zuke-no-moto" to obtain "bettara-zuke", fresh radish pickles. The product has an excellent color, gloss and flavor, moderate sweetness, and superior crispness, and further is less acidified and stable over an extended storage.

EXAMPLE B-14

Intubation feeding

A composition consisting of 20 parts by weight of a high-purity hydrous crystalline maltosyl glucoside obtained by the method in Example A-1, 1.1 parts by weight of glycine, 1 part by weight of sodium glutamate, 0.4 parts by weight of calcium lactate, 0.1 part by weight of magnesium carbonate, 0.01 part by weight of thiamine and 0.01 part by weight of riboflavin was prepared, and the composition was divided into 24 g aliquot in small laminated aluminum packs which were then heat-sealed. One pack of the product is dissolved in about 300–500 ml water and the resultant solution is usable as a liquid supplemental nutrition which can be administered to the nasal cavity, stomach or intestine by intubation feeding. The product is also favorably usable as a parenteral liquid supplemental nutrition for domestic animals.

EXAMPLE B-15

Intubation feeding

A composition consisting of 580 parts by weight of a high-purity hydrous crystalline maltosyl glucoside obtained by the method in Example A-2, 190 parts by weight of dried yolk, 209 parts by weight of defatted milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate and 0.04 parts by weight of nicotine amide was prepared, and the composition was divided into 25 g aliquot in small laminated aluminum packs which were then heat-sealed. One pack of the product is dissolved in about 150–300 ml water and the resultant solution is usable as an a liquid supplemental nutrition parenterally administrable to the nasal cavity, stomach or intestine.

EXAMPLE B-16

Traumatic ointment

Three hundred parts by weight of high-purity hydrous crystalline maltosyl glucoside obtained by the method in Example A-1 and 200 parts by weight of crystalline maltose were admixed with 5 parts by weight of methanol containing 3 parts by weight of iodine, and the resultant was mixed with 200 parts by weight of 10% pullulan to obtain a traumatic ointment which has an appropriate extensibility and adhesiveness. The product shortens a therapeutic period and cure traumas without a scar.

EXAMPLE B-17

Liquid interferon agent

A natural human interferon-γ preparation, produced by Hayashibara Biochemical Laboratories, Inc., Okayama, Japan and commercialized by Cosmo Bio Co., Ltd., Tokyo, Japan, was subjected in the usual manner to an immobilized anti-human interferon-γ antibody column to adsorb thereto the natural human interferon-γ in the preparation, and the calf serum albumin as stabilizer was passed through the column, and the natural human interferon-γ adsorbed on the antibody was eluted by using a physiological saline which contained a high-purity hydrous crystalline maltosyl glucoside obtained by the method in Example A-1 in an amount of 7%, while changing the pH of the saline. Thereafter the eluate was subjected to membrane filtration and sterilely bottled in vials to obtain a liquid agent which contained $10^5$ units/ml of natural human interferon-γ. The liquid agent is favorably usable in the treatment of viral diseases, allergic diseases, rheumatism, diabetes and malignant tumors where the liquid agent is perorally or parenterally administered at a dose of 1–20 ml/day/adult. The liquid agent retains its initial activity even when allowed to stand at 4° C. or 25° C. for 20 days because maltosyl glucoside acts as stabilizer.

EXAMPLE B-18

Liquid tumor necrosis factor agent

A natural human tumor necrosis factor-α preparation, produced by Hayashibara Biochemical Laboratories, Inc., Okayama, Japan and commercialized by Cosmo Bio Co., Ltd., Tokyo, Japan, was subjected in the usual manner to an immobilized anti-human tumor necrosis factor-α antibody column to adsorb thereto the natural human tumor necrosis factor-α in the preparation, and the calf serum albumin as stabilizer was passed through the column, and the natural human tumor necrosis factor-α adsorbed on the antibody was eluted by using a physiological saline containing a high-purity hydrous crystalline maltosyl glucoside obtained by the method in Example A-1 in an amount of 10%, while changing the pH of the saline. Thereafter the eluate was subjected to membrane filtration and sterilely bottled in vials to obtain a liquid agent which contained $10^4$ units/ml of natural human tumor necrosis factor-α. The liquid agent is favorably usable in the treatment of viral diseases, allergic diseases, rheumatism, diabetes and malignant tumors where the liquid agent is perorally or parenterally administered at a dose of 1–20 ml/day/adult. The liquid agent retains its initial activity even when allowed to stand at 4° C. or 25° C. for 20 days because maltosyl glucoside acts as stabilizer.

EXAMPLE B-19

Interferon tablet

A natural human interferon-α preparation, produced by Hayashibara Biochemical Laboratories, Inc., Okayama, Japan and commercialized by Cosmo Bio Co., Ltd., Tokyo, Japan, was subjected in usual manner to an immobilized anti-human interferon-α antibody column to adsorb thereto the natural human interferon-α in the preparation, and the calf serum albumin as stabilizer was passed through the column for removal, and the natural human interferon-α adsorbed on the antibody was eluted by using a physiological saline which contained a high-purity hydrous crystalline maltosyl glucoside obtained by the method in Example A-1 in an amount of 5%, while changing the pH of the saline. Thereafter the resultant eluate was subjected to membrane filtration, dehydrated and pulverized by the addition of about 20-fold amount of "FINETOSE® T", a crystalline anhydrous maltose powder commercialized by Hayashibara Shoji Co., Ltd., Okayama, Japan and the resultant powder was fed to tabletting machine to obtain tablets (about 200 mg each) which contained about 150 units/tablet of natural human interferon-α. The tablet is favorably usable as lozenge in the treatment of viral diseases, allergic diseases, rheumatism, diabetes and malignant tumors where the tablet is perorally administered at a dose of about 1–10 tablets/day/adult. In particular, the tablet is favorably usable as therapeutic agent for AIDS and hepatitis patients which have been rapidly increasing in recent years. The tablet retains its initial activity over an extended time period even when allowed to stand at room temperature because maltosyl glucoside acts together with crystalline anhydrous maltose as stabilizer.

EXAMPLE B-20

Sugar coated tablet

An crude tablet having 150 mg weight was sugar-coated by using a solution containing 45 parts by weight of high-purity hydrous crystalline maltosyl glucoside obtained by the method in Example A-2, 2 parts by weight of pullulan (average molecular weight: 200,000), 30 parts by weight of water, 25 parts by weight of talc and 3 parts by weight of titanium oxide until the weight of tablet increases to about 230 mg, and further sugar-coated by a solution containing 65 parts by weight of hydrous crystalline maltosyl glucoside powder, 1 part by weight of pullulan and 34 parts by weight of water, and glossed with a polishing wax to obtain a sugar coated tablet which has a glossy appearance. The product is excellent in efficiency for sugar-coating process and impact-resisting, and remains its high quality over an extended shortage.

EXAMLPLE B-21

Milky lotion

One half parts by weight of polyoxyethylene behenyl ether, 1 part by weight of polyoxyethylene sorbitol tetraoleate, 1 part by weight of oil-soluble glycerol monostearate, 0.5 parts by weight of behenyl alcohol, 1 part by weight of avocado oil, 3.5 parts by weight of a high-purity hydrous crystalline maltosyl glucoside obtained by the method in Example A-2, 1 part by weight of α-glycosyl rutin and appropriate amounts of vitamin E and germicidal agent were dissolved in usual manner by heating, and the mixture was admixed with 5 parts by weight of 1,3-butylene glycol, 0.1 part by weight of carboxyvinyl polymer and 85.3 parts by weight of refined water and emulsified with homogenizer to obtain milky lotion. The product is a moisture-retaining milky lotion which is favorably usable as sunscreen and skin-whitening agent.

EXAMPLE B-22

Skin cream

Two parts by weight of polyoxyethylene glycol monostearate, 5 parts by weight of self-emulsifying glycerine monostearate, 2 parts by weight of α-glycosyl rutin, 1 part by weight of liquid paraffin, 10 parts by weight of glyceryl trioctanate, 4 parts by weight of high-purity hydrous crystalline maltosyl glucoside obtained by the method in Example A-1, 3 parts by weight of maltitol and an appropriate amount of antiseptic were dissolved in usual manner by heating, and the resultant solution was admixed with 5 parts by weight of 1,3-butylene glycol and 66 parts by weight of refined water, emulsified with homogenizer and admixed with an appropriate amount of flavoring agent by stirring to obtain skin cream. The product is a well-spreading cream which is favorably usable as a cream of sunscreen, skin-refining agent or skin-whitening agent.

EXAMPLE B-23

Dentifrice

Forty-five parts by weight of calcium hydrogen phosphate, 1.5 parts by weight of sodium laurate, 25 parts by weight of glycerine, 0.5 parts by weight of polyoxyethylene sorbitan laurate, 15 parts by weight of a high-purity hydrous crystalline maltosyl glucoside obtained by the method in Example A-2, 0.02 parts by weight of saccharin and 0.05 parts by weight of antiseptic were admixed with 13 parts by weight of water to obtain dentifrice. The product, having a superior gloss and detergency, is suitable as dentifrice.

EXAMPLE B-24

Fertilizer rod

Fertilizer composition (N=14%, $P_2O_5$=8%, $K_2O$=12%), pullulan, a powder containing hydrous crystalline maltosyl glucoside obtained by the method in Example A-6, calcium sulfate and water were mixed in the weight of 70, 5, 5, 15 and 5 respectively, and the resultant mixture was fed to an extruder (L/D=20, suppress ratio =1.8, dice diameter =30 mm) while heating at 80° C. to obtain a fertilizer rod. The product is handleable without a vessel for fertilizer and has an appropriate hardness for total layer application, and can be adjusted its melting speed by arranging the composition ratio. If necessary, the product can be readily admixed with plant hormones, agricultural chemicals and soil conditioners.

As evident from the above description, the crystalline maltosyl glucoside of this invention is a substance which is non-hygroscopic, non-reducing, readily handleable with superior fluidity, readily soluble in water and has an appropriate viscidity as well as superior sweetness. Further the crystalline maltosyl glucoside of this invention has a chemical stability and properties of stabilizing amino acids and oligopeptides which readily cause browning reaction, as well as properties of stabilizing biologically-active substances whose activity or active ingredient readily inactivates. Still further the crystalline maltosyl glucoside of this invention has additional features of controlling osmotic pressure, activating property, imparting gloss, retaining moisture, having an appropriate viscosity, preventing crystallization of other saccharides, having less fermentability and preventing retrogradation of amylaceous substances. These features are favorably utilizable in the production of various compositions including foods, beverages, cosmetics, pharmaceuticals.

Thus the establishment of crystalline maltosyl glucoside according to this invention and its production and use would have an industrial significance in the field of foods, beverages, cosmetics and pharmaceuticals.

We claim:

1. A purified crystalline maltosyl glucoside, which is sufficiently pure to exhibit a melting point of 180° C. and X-ray diffraction data and which is a member selected from the group consisting of hydrous crystalline maltosyl glucoside having predominant diffraction angles 2θ of 7.9°, 13.2°, 17.2° and 22.6° on powder X-ray diffraction analysis, anhydrous crystalline maltosyl glucoside having predominant diffraction angles 2θ of 7.7°, 13.5°, 17.6°, and 23.6° on powder X-ray diffraction analysis, and mixtures thereof, said crystalline maltosyl glucoside being hydrolyzed into glucose and trehalose when contacted with glucoamylase and being hydrolyzed into D-glucose when hydrolyzed by 1N sulfuric acid, and having a satisfactory free-flowing ability and melting point of 180° C.

2. A solid saccharide composition consisting essentially of a mixture of the hydrous and anhydrous crystalline maltosyl glucosides of claim 1.

3. In a solid composition which contains crystalline maltosyl glucoside the improvement wherein said solid composition is prepared by using the high purity crystalline maltosyl glucoside of claim 1 as the maltosyl glucoside.

4. The solid composition of claim 3, wherein said high purity crystalline maltosyl glucoside is incorporated in an amount at least 0.1 w/w %, on a dry solid basis.

5. The solid composition of claim 3, wherein said solid composition is a food, cosmetic pharmaceutical.

6. A process for preparing the high-purity crystalline maltosyl glucoside of claim 1 which comprises:

(a) adding a seed of crystalline maltosyl glucoside in a sufficient amount to crystallize maltosyl glucoside from a solution of maltosyl glucoside;

(b) purifying the crystallized maltosyl glucoside; and (c) recovering the resultant purified crystalline maltosyl glucoside, wherein said maltosyl glucoside in step (a) is prepared by treating an aqueous solution of trehalose and an α-glucosyl saccharide with a saccharide-transferring enzyme or with a saccharide-transferring enzyme followed by treating said aqueous solution of trehalose and an α-glucosyl saccharide with a hydrolase; or by treating a reducing partial starch hydrolysate with a non-reducing saccharide-forming enzyme or by treating a reducing partial starch hydrolysate with a non-reducing saccharide-forming enzyme and then treating the reducing partial starch hydrolysate with a hydrolase; said saccharide-transferring enzyme being selected from the group consisting of cyclomaltodextrin glucotransferase, α-amylase, α-glucosidase, and mixtures thereof.

7. The process of claim 6, wherein said hydrolase is a member selected from the group consisting of β-amylase and a mixture of β-amylase and a starch-debranching enzyme.

8. The process of claim 6, wherein said non-reducing saccharide-forming enzyme is an enzyme derived from a microorganism selected from the group consisting of Rhizobium M-11 FERM BP-4130; Arthrobacter sp. Q36 FERM BP-431 *Brevibacterium helovolum,* ATCC 11822; *Flavobacterium aguatile,* IFO 3772; *Miocrococcus luteus,* IFO 3064; *Micrococcus roseus.* ATCC 186; *Curtobacterium citrem,* IFO 15231; *Mycobacterium smegmatis,* ATCC 19420; and *Terrabacter tumescens,* IFO 12960, which enzymes are capable of forming a non-reducing saccharide which has a trehalose structure as an end unit from a reducing partial starch hydrolysate.

9. The process of claim 6, wherein said reducing partial starch hydrolysate has a glucose polymerization degree of 3 or higher.

10. The process of claim 8, wherein said reducing partial starch hydrolysate has a glucose polymerization degree of 3 or higher.

11. A process for preparing the high purity crystalline maltosyl glucoside of claim 1, which comprises:
  (a) alkali-treating an aqueous solution containing maltosyl glucoside; and
  (b) applying the resultant solution to a column chromatography to obtain a fraction rich in maltosyl glucoside; and
  (c) concentrating and crystallizing the fraction; and
  (d) recovering the resultant crystalline maltosyl glucoside.

12. The process of claim 11, wherein said aqueous solution in the step (a) is obtained by treating an aqueous solution containing trehalose and an α-glucose saccharide with a saccharide-transferring enzyme or with a saccharide-transferring enzyme and then a hydrolase in this order; or by treating a reducing partial starch hydrolysate with a non-reducing saccharide forming enzyme or with a non-reducing saccharide-forming enzyme and then a hydrolase in this order.

13. The process of claim 12, wherein said saccharide-transferring enzyme is a member selected from the group consisting of cyclomaltodextrin glucanotransferase, α-amylase, α-glucosidase, and mixtures thereof.

14. The process of claim 12, wherein said hydrolase is a member selected from the group consisting of β-amylase and a mixture of β-amylase and a starch-debranching enzyme.

15. The process of claim 12, wherein said non-reducing saccharide-forming enzyme is an enzyme derived from a microorganism selected from the group consisting of Rhizobium M-11 FERM BP-4130; Arthrobacter sp. Q35 FERM BP-4316 *Brevibacterium helovolum,* ATCC 11822; *Flavobacterium aguatile,* IFO 3772; *Miocrococcus luteus*, IFO 3064; *Micrococcus roseus.* ATCC 186; *Curtobacterium citrem,* IFO 15231; *Mycobacterium smegmatis*, ATCC 19420; and *Terrabacter tumescens*, IFO 12960, which enzymes are capable of forming a non-reducing saccharide which has a trehalose structure as an end unit from a reducing partial starch hydrolysate.

16. The process of claim 12, wherein said reducing partial starch hydrolysate has a glucose polymerization degree of 3 or higher.

17. The process of claim 15, wherein said reducing partial starch hydrolysate has a glucose polymerization degree of 3 or higher.

18. In a process for preparing a solid composition containing maltosyl glucoside, the improvement comprising using the crystalline maltosyl glucoside of claim 1 as the maltosyl glucoside.

19. The process of claim 18, wherein said composition contains said crystalline maltosyl glucoside in an amount at least 0.1 w/w %, on a dry solid basis.

20. The process of claim 18, wherein said composition is a member selected from the group consisting of foods, beverages, cosmetics, and pharmaceuticals.

* * * * *